United States Patent
Schofield et al.

(10) Patent No.: US 9,422,589 B2
(45) Date of Patent: Aug. 23, 2016

(54) ASSAY FOR HISTIDINYL HYDROXYLASE ACTIVITY

(75) Inventors: Christopher Joseph Schofield, Oxford (GB); Wei Ge, Oxford (GB); Matthew Edward Cockman, Oxford (GB); Peter John Ratcliffe, Oxford (GB); Mathew Louis Coleman, Oxford (GB)

(73) Assignee: Isis Innovation Limited, Oxford (GB)

( * ) Notice: Subject to any disclaimer, the term of this patent is extended or adjusted under 35 U.S.C. 154(b) by 86 days.

(21) Appl. No.: 14/235,217

(22) PCT Filed: Jul. 25, 2012

(86) PCT No.: PCT/GB2012/051784
§ 371 (c)(1),
(2), (4) Date: May 7, 2014

(87) PCT Pub. No.: WO2013/014449
PCT Pub. Date: Jan. 31, 2013

(65) Prior Publication Data
US 2014/0248636 A1    Sep. 4, 2014

(30) Foreign Application Priority Data
Jul. 28, 2011    (GB) .................................. 1113101.8

(51) Int. Cl.
*C12Q 1/26*    (2006.01)
*G01N 33/50*    (2006.01)
*G01N 33/573*    (2006.01)

(52) U.S. Cl.
CPC .............. *C12Q 1/26* (2013.01); *G01N 33/5023* (2013.01); *G01N 33/573* (2013.01); *G01N 2333/90245* (2013.01)

(58) Field of Classification Search
None
See application file for complete search history.

(56) References Cited

U.S. PATENT DOCUMENTS

2005/0214894 A1    9/2005    Schofield et al.

FOREIGN PATENT DOCUMENTS

WO    WO-2005/093411 A2    10/2005
WO    WO-2007/034214 A1    3/2007

OTHER PUBLICATIONS

Teye et al., "Increased Expression of a Myc Target Gene Mina53 in Human Colon Cancer", American Journal of Pathology, Jan. 2004, vol. 164, No. 1, pp. 205-216.*
Eilbracht et al., "NO66, a highly conserved dual location protein in the nucleolus and in a special type of synchronously replicating chromatin," Mol Biol Cell. 15(4):1816-32 (2004).
Sinha et al., "Regulation of the osteoblast-specific transcription factor Osterix by NO66, a Jumonji family histone demethylase," EMBO J. 29(1):68-79 (2010).
Tsuneoka et al., "A novel myc target gene, mina53, that is involved in cell proliferation," J Biol Chem. 277(38):35450-9 (2002).
Yang et al., "Factor-inhibiting hypoxia-inducible factor (FIH) catalyses the post-translational hydroxylation of histidinyl residues within ankyrin repeat domains," FEBS J. 278(7):1086-97 (2011).
International Search Report and Written Opinion for International Application No. PCT/GB2012/051784, dated Jan. 17, 2013 (9 pages).

* cited by examiner

*Primary Examiner* — Suzanne M Noakes
(74) *Attorney, Agent, or Firm* — Clark & Elbing LLP; Susan M. Michaud

(57) ABSTRACT

The present invention relates to assays for monitoring activity of Mina53 and NO66 activities, in particular, to assays for identifying modulators of Mina53 and NO66 activities. The invention also relates to assays to monitor the histidinyl hydroxylase activity of Mina53 and NO66 on their substrates, the human ribosomal protein Rpl27a and Rpl8 respectively. The invention also enables the introduction of S-3-hydroxyhistidinyl residues into peptides and proteins.

11 Claims, 10 Drawing Sheets

Fig. 1   Sequence alignment of FIH, Mina53 and NO66

```
FIH   : ------------------------------------MAATAAEAVASGSGEPREEA----------------GAIGPAWDESQLRSYSFPTRP  :  41
Mina  : -------------------------------------MPKKAKPTGSGKEEGPAPCKQMKLEAAGGPSALNFDSPSSLFESLISPIKT       :  51
NO66  : ALLCTAQHLAAVQSSGAPATASGPQ-VDNTG-GEPAWDSPLRRVLAELNRIPSSRR--RAARLFEWLIAPMPP                      : 215

FIH   : IPRLSQSDPRAEELENEEPVLIDTNLVYPALKWDLEYLQENIGNGDFSVYSASTHKFLYDEKKMANEQNF                         : 114
Mina  : ETFFKEFWEQKPILIQRDDPALAT------YYGSTFKLTDLKS-LCSRGMY----------YGRDVNVCRCMNG                    : 108
NO66  : DHEYRRLWEREAVLVRQD----HT------YLQGLFSTADLDSMLRNEEVQ---------EGQHLDAARYING                     : 270

FIH   : KPRSNREMKFHEFVERLQDIQQRGGERLYLQQTLNDTVGRKIVMDFLGFNWMWINKQQGKRGWGQLT-SNL                        : 186
Mina  : KKKVLNKDGKAHFLQLRKDFDQKRATIQFHQPQRFKDEI-----------------------WRIQEKLECYFGSLVGSNV             : 166
NO66  : RRFTLNPPGRA--LPAAAWSLYQAGCSIRLLCEQAFSTTV--------------------WQFLAVLQEQGSMAGSNV                : 327

FIH   : LIIGMEGNVTPAHYDEQQNFEAQIKGYKRCILFPPDQFECLYPYP---VHHPCDRQSQVDFDNPDYERFPNFQ                     : 256
Mina  : YIITPAGSQGLPHYDDVEVFILQLEGEKHWRLYHP----TVP----LAREYSVE-AERIGRPV                               : 221
NO66  : YLIPPNSQGFAHYDDIEAEVILQIEGRKLMRVYRP----------RVPTEELALTSSPNFSQDLGEPV                          : 386

FIH   : NVVGYEIVVGPGDVLYIPMYWWHIESL----INGGITTVNFWYKGA----------------------------------PTP           : 303
Mina  : -----HEFMIKPGLLYFPRGTIHQADIPAGLAHSTHVTISTYQNNSWGDFLDTISGEVFDTA-KEDVELRTG                      : 289
NO66  : -LQHVFPGDLLYFERGFIHQAECQDGV-HSLHLTLSTYQRNTWGDEL-EAILPLAVQAAMENVEFRG                           : 453

FIH   : KRIEYP---LKAHQKVAIMRNLEKML----------------------------------GEALGNPQE                         : 335
Mina  : IPRQLL--IQVESTVATRRLSGFL-----RTLADRIE--GTKELISSDMKKDFIMHRLPPYSAGDCAEISTPGG                    : 355
NO66  : LPRDFMDYMGAQHSDSKDPRRTAHMEKVRLVARIGHFAPVDAVADQRAKDEIHDSLPPVLTDRERALSVYG-                      : 525

FIH   : VGPLLNTMIKGRYN-----------------------------------                                             : 349
Mina  : KIP-RLDS---V-VRLQFKDHIVETVIPDQDQSDEAQEKMVYIHSLKNSRETHMGNEETEFHGIRFPLSH                        : 423
NO66  : -LPIRWEAGEPVNVGAQLTTETEVHMLQDGIARLVGEGGHLFLYTVENSRVYHI-----EEPKCLEI-YF-QQ                     : 591

FIH   : -                                                                            :  -
Mina  : LDAIKQIWNS-PA-ISVKDIKLTEDEKESVLSMWTECLIQVV-----                               : 465
NO66  : ADAMELLGSYPEFVRVGDLPCDSVEDQLSIATILYDKGLLLTKMPLAIN-                            : 641
```

Fig. 3
LCMS and MSMS spetra of RpL27a tryptic peptide
GNAGGLHHHR $[M+2H]^{2+}$
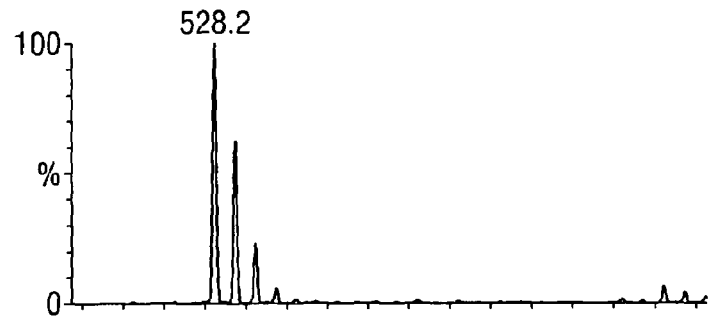
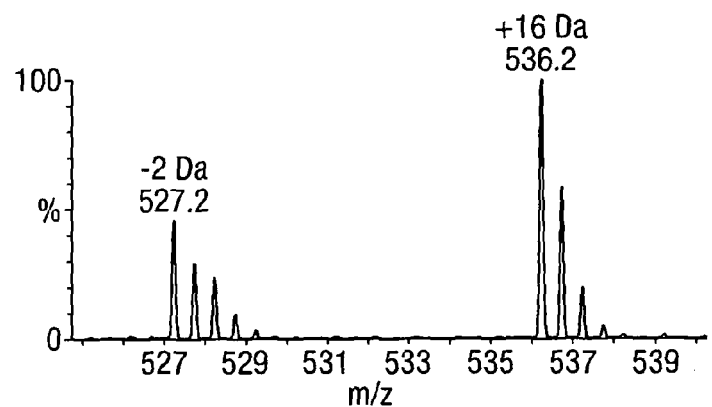
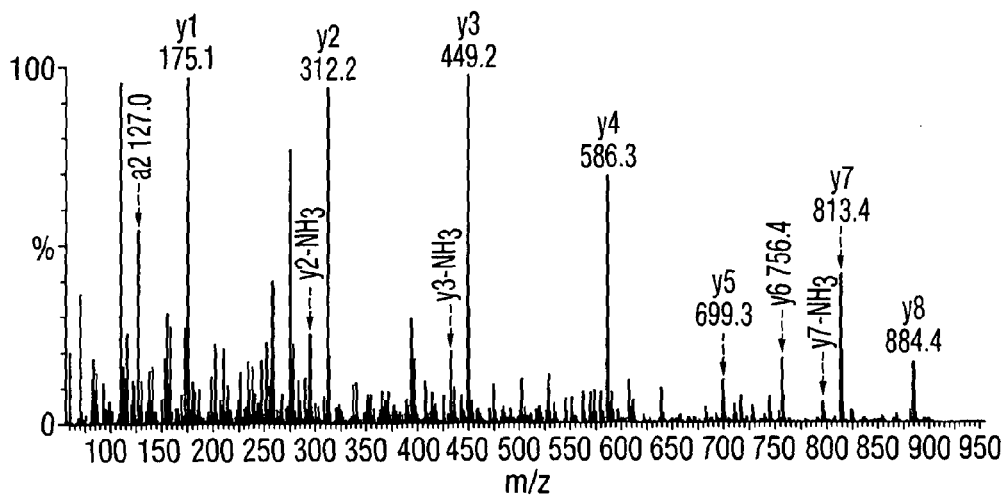

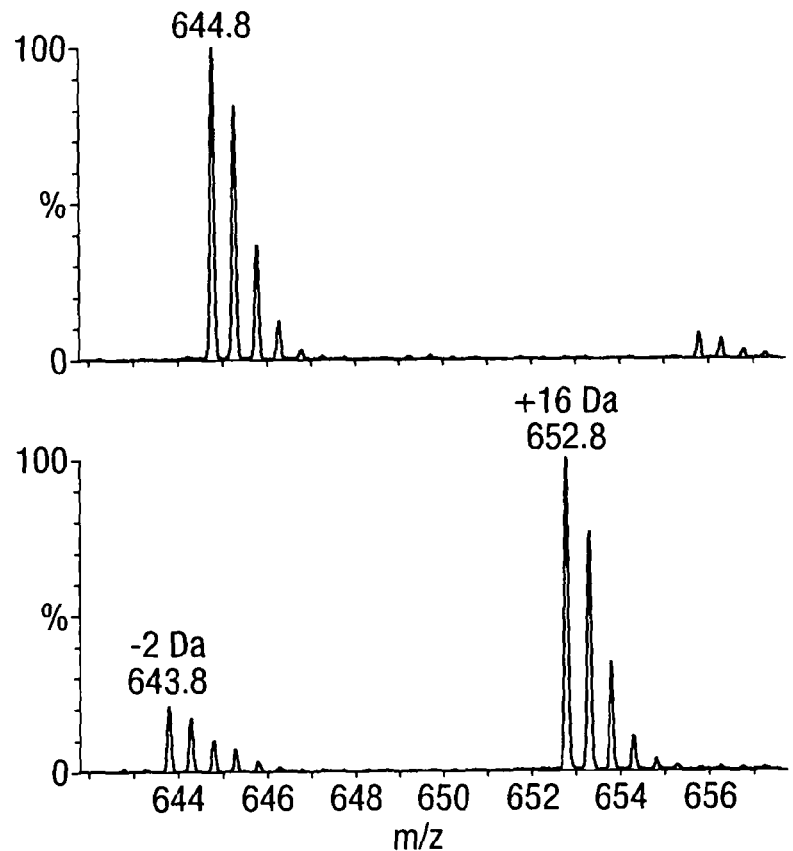

Fig. 6    Endogenous Rpl8 is Hydroxylated at His-216

| | | b+ | b++ | y+ | y++ | | |
|---|---|---|---|---|---|---|---|
| G | 1 | 58.03 | 29.52 | | | 26 | G |
| V | 2 | 157.10 | 79.05 | 2680.35 | 1340.68 | 25 | V |
| A | 3 | 228.13 | 114.57 | 2581.28 | 1291.15 | 24 | A |
| M | 4 | 359.17 | 180.09 | 2510.25 | 1255.63 | 23 | M |
| N | 5 | 473.22 | 237.11 | 2379.21 | 1190.11 | 22 | N |
| P | 6 | 570.27 | 285.64 | 2265.16 | 1133.09 | 21 | P |
| V | 7 | 669.34 | 335.17 | 2168.11 | 1084.56 | 20 | V |
| E | 8 | 798.38 | 399.69 | 2069.04 | 1035.02 | 19 | E |
| H | 9 | 935.44 | 468.22 | 1940.00 | 970.50 | 18 | H |
| P | 10 | 1032.49 | 516.75 | 1802.94 | 901.97 | 17 | P |
| F | 11 | 1179.56 | 590.28 | 1705.89 | 853.45 | 16 | F |
| G | 12 | 1236.58 | 618.80 | 1558.82 | 779.91 | 15 | G |
| G | 13 | 1293.60 | 647.31 | 1501.80 | 751.40 | 14 | G |
| G | 14 | 1350.63 | 675.82 | 1444.78 | 722.89 | 13 | G |
| N | 15 | 1464.67 | 732.84 | 1387.76 | 694.38 | 12 | N |
| H | 16 | 1601.73 | 801.37 | 1273.71 | 637.36 | 11 | H |
| Q | 17 | 1729.79 | 865.40 | 1136.65 | 568.83 | 10 | Q |
| H | 18 | 1866.85 | 933.93 | 1008.59 | 504.80 | 9 | H |
| I | 19 | 1979.93 | 990.47 | 871.54 | 436.27 | 8 | I |
| G | 20 | 2036.95 | 1018.98 | 758.45 | 379.73 | 7 | G |
| K | 21 | 2165.05 | 1083.03 | 701.43 | 351.22 | 6 | K |
| P | 22 | 2262.10 | 1131.55 | 573.34 | 287.17 | 5 | P |
| S | 23 | 2349.13 | 1175.07 | 476.28 | 238.65 | 4 | S |
| T | 24 | 2450.18 | 1225.59 | 389.25 | 195.13 | 3 | T |
| I | 25 | 2563.26 | 1282.13 | 288.20 | 144.61 | 2 | I |
| R | 26 | | | 175.12 | 88.06 | 1 | R |

| | | b+ | b++ | y+ | y++ | | |
|---|---|---|---|---|---|---|---|
| G | 1 | 58.03 | 29.52 | | | 26 | G |
| V | 2 | 157.10 | 79.05 | 2696.35 | 1348.68 | 25 | V |
| A | 3 | 228.13 | 114.57 | 2597.28 | 1299.14 | 24 | A |
| M | 4 | 359.17 | 180.09 | 2526.24 | 1263.62 | 23 | M |
| N | 5 | 473.22 | 237.11 | 2395.20 | 1198.10 | 22 | N |
| P | 6 | 570.27 | 285.64 | 2281.16 | 1141.08 | 21 | P |
| V | 7 | 669.34 | 335.17 | 2184.11 | 1092.56 | 20 | V |
| E | 8 | 798.38 | 399.69 | 2085.04 | 1043.02 | 19 | E |
| H | 9 | 935.44 | 468.22 | 1955.99 | 978.50 | 18 | H |
| P | 10 | 1032.49 | 516.75 | 1818.94 | 909.97 | 17 | P |
| F | 11 | 1179.56 | 590.28 | 1721.88 | 861.45 | 16 | F |
| G | 12 | 1236.58 | 618.80 | 1574.81 | 787.91 | 15 | G |
| G | 13 | 1293.60 | 647.31 | 1517.79 | 759.40 | 14 | G |
| G | 14 | 1350.63 | 675.82 | 1460.77 | 730.89 | 13 | G |
| N | 15 | 1464.67 | 732.84 | 1403.75 | 702.38 | 12 | N |
| H | 16 | 1617.72 | 809.36 | 1289.71 | 645.36 | 11 | H |
| Q | 17 | 1745.78 | 873.39 | 1136.65 | 568.83 | 10 | Q |
| H | 18 | 1882.84 | 941.92 | 1008.59 | 504.80 | 9 | H |
| I | 19 | 1995.92 | 998.47 | 871.54 | 436.27 | 8 | I |
| G | 20 | 2052.95 | 1026.98 | 758.45 | 379.73 | 7 | G |
| K | 21 | 2181.04 | 1091.02 | 701.43 | 351.22 | 6 | K |
| P | 22 | 2278.09 | 1139.55 | 573.34 | 287.17 | 5 | P |
| S | 23 | 2365.13 | 1183.07 | 476.28 | 238.65 | 4 | S |
| T | 24 | 2466.17 | 1233.59 | 389.25 | 195.13 | 3 | T |
| I | 25 | 2579.26 | 1290.13 | 288.20 | 144.61 | 2 | I |
| R | 26 | | | 175.12 | 88.06 | 1 | R |

Fig. 6(Cont I).

GVAMNPVEHPFGGGNH(+15.99)QHIGKPSTIR

Charge: 3, Exp. m/z: 918.458, Calc. m/z: 918.461
Data File: LTQ0047_YL249, Scans: 5223 - 5223

Max Intensity: 1.55e+05

GVAMNPVEHPFGGGNHQHIGKPSTIR

Charge: 3, Exp. m/z: 913.130, Calc. m/z: 913.127
Data File: LTQ0047_YL249, Scans: 5560 - 5560

Max Intensity: 1.48e+05

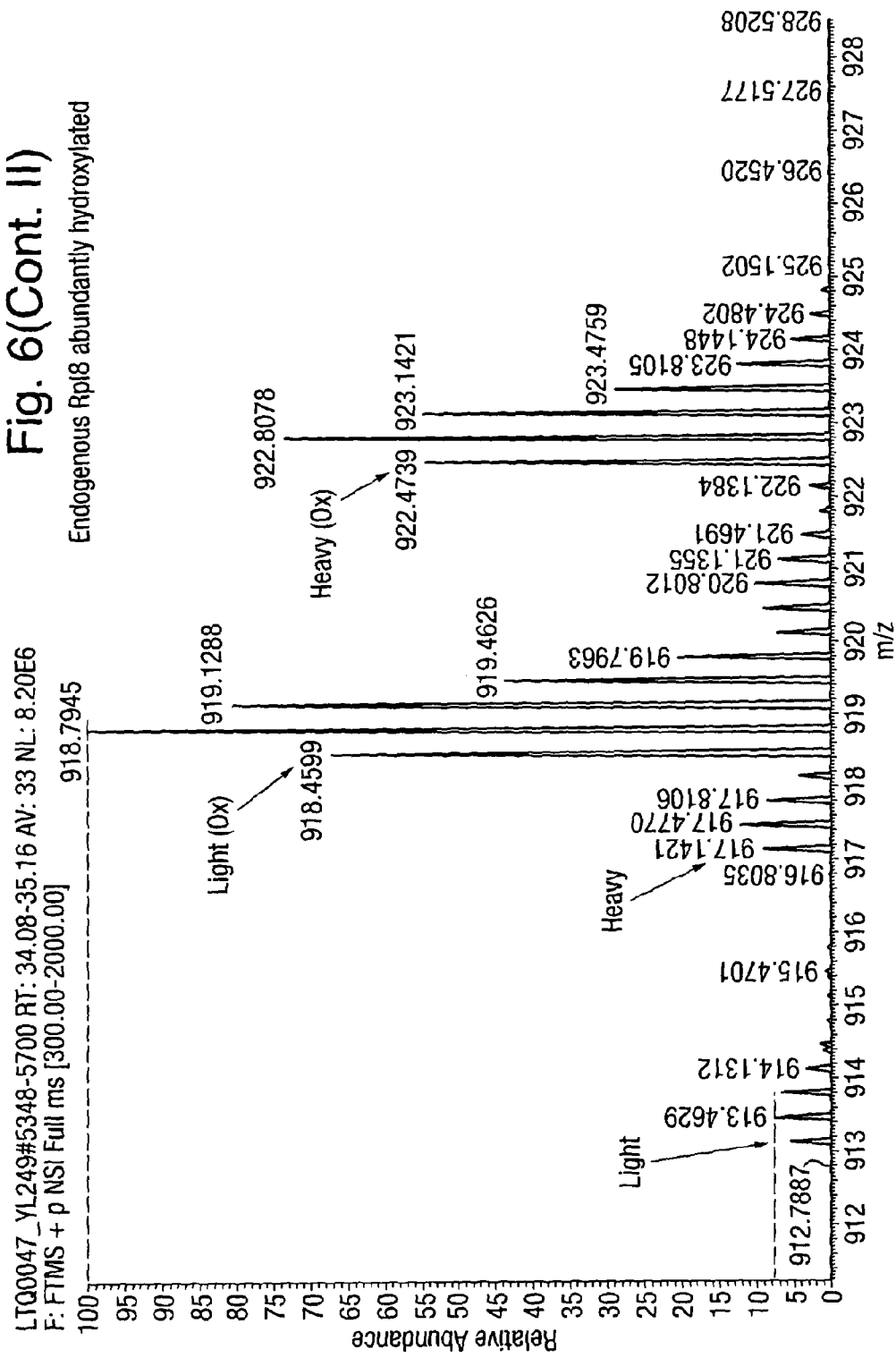
Fig. 6(Cont. II)
Endogenous Rpl8 abundantly hydroxylated ns, a hydroxyl group, or in the
case of N-methyl group hydroxylation, the formation of an
unstable intermediate that decomposes into formaldehyde.
The latter reaction is employed by 2OG-oxygenases that
catalyse N-demethylation reactions of nucleic acids and proteins.

The human genome contains approximately 60 genes predicted to encode 2OG-oxygenases, many of which are not characterised in terms of their substrates. Proteins of this gene family can be subdivided into groups based on similarity within the catalytic motif. For example, the Hypoxia Inducible Factor (HIF) prolyl hydroxylases consists of three 2OG-hydroxylases (PHD1-3 or EGLN1-3 enzymes) that target the Hypoxia Inducible transcription Factor (HIF) for proteolytic degradation. The JmjC histone demethylase subfamily members catalyse the demethylation of specific lysine residues within the N-terminal tails of histone proteins and are involved in the regulation of chromatin structure and gene expression.

The Factor Inhibiting HIF (FIH), is an asparaginyl hydroxylase that, like PHD1-3, also targets HIF. FIH-mediated hydroxylation of the HIF C-terminal transactivation domain (CAD) mediates oxygen-sensitive regulation at the transcriptional activity. Recently, it was reported that FIH catalyses the hydroxylation of histidinyl residues within the ankrin repeat domains. FIH is one of a family of human 2OG oxygenases related to the Jmjc subfamily. Other members of this family that have been assigned 2OG-oxygenase activity include JMJD6. Although comparatively little is known about the activity and function of the FIH sub-group of 2OG-oxygenases (compared to the PHD1-3 or Jmjc subfamily), they are of significant interest due to the fact that they are implicated in pathological processes in cells, or are abnormally expressed in disease, and particularly in cancer.

MINA53 is a 2OG/Fe(II)-dependent dioxygenase originally identified in a microarray screen for Myc target genes overexpressed in glioblastoma cells. MINA53 overexpression was subsequently observed in a variety of tumour types and is often associated with poor prognosis. MINA53 has been implicated in several biological and pathologically relevant processes implicated in tumourigenesis, including cell proliferation, apoptosis, and invasion. MINA53 shares significant sequence homology with a closely related human 2OG/Fe(II)-dependent dioxygenase known as NO66. Like MINA53, NO66 has also been implicated in cancer: It is overexpressed in non-small cell lung cancer and it regulates apoptosis and proliferation in vitro Tsuneoka et al, J. Biological Chem 2002, 277, 35450-35459, Komiya et al, J. Cancer Res Clin Oncol, 2010, 136, 465-473, Stry et al, Nat Immunol, 2009, 872-879.

MINA53 and NO66 are primarily localised to the nucleolus and are negatively regulated by mitogen withdrawal and RNA Polymerase I inhibition. Proteomic analyses identify these enzymes in complex with a variety of ribosomal and nucleolar proteins. Together, these observations implicate MINA53/NO66 in ribosomal biogenesis/function and/or protein translation: Over-activation of these processes are hallmarks of tumour cells, Eilbracht et al, Mol Biology of the Cell, 2004, 15, 1816-1832, Sinha et al, EMBO J, 2010, 29, 68-79.

SUMMARY OF THE INVENTION

The present inventors have identified that Mina53 and NO66 are 2OG oxygenases, and specifically, that they are beta-carbon histidinyl-hydroxylases. Substrates for Mina53 and NO66 are identified as human ribosomal proteins, Rpl27a and Rpl8, respectively. Accordingly, the present invention provides a method for assaying Mina53 and NO66 activity, the method comprising contacting a peptide containing a histidinyl-residue, with a Mina53 or NO66 polypeptide and determining whether the histidinyl-residue in said peptide is hydroxylated. The invention also provides a method for identifying an inhibitor or activator of Mina53 or NO66 oxygenase activity, the method comprising contacting a Mina53 or NO66 polypeptide and a histidinyl-residue containing peptide with a test agent under conditions suitable for oxygenase activity, and monitoring for hydroxylation of said peptide.

The invention further provides a method for identifying a modulator of protein translation, the method comprising contacting a cell which expresses Mina53 or NO66 with a test agent and determining whether the test agent modulates the Mina53 or NO66 mediated regulation of protein translation.

The invention further provides an inhibitor or activator of 2OG oxygenase activity for use in modulating histidinyl-hydroxylation by Mina53 or NO66 of a ribosomal protein or a fragment or variant thereof comprising a histidinyl-residue, or for use in modulating protein translation.

BRIEF DESCRIPTION OF THE FIGURES

FIG. 1: Sequence alignment of Mina53 and NO66 and FIH. Human FIH (gi|32129605) (SEQ ID NO: 3), Mina53 (gi|23307412) (SEQ ID NO: 1) and NO66 (gi|106879206) (amino acids 147-641 of SEQ ID NO: 2) sequences were aligned and shaded using ClustalW and BoxShade servers.

FIG. 6: Endogenous Rpl8 H216 hydroxylation is dependent on NO66. Ribosomal proteins were purified from doxycyline-treated doxycycline-inducible pTRIBZ control ShRNA or NO66 ShRNA A549 and HeLa cells as described. Rpl8 was separated from other ribosomal proteins by HPLC, lyophilized and subject to in-solution trypsinolysis and MS analysis. A) MSMS spectra of the unhydroxylated (left) and hydroxylated (right) GVAMNPVEHPFGGGNHQHIGKP-STIR (SEQ ID NO:10) tryptic peptides. The hydroxlated species exhibits a +16 Da mass shift on the y-ion series appearing at y16, thus assigning hydroxylation to H216. B) i) LC-MS spectra of unoxidised and oxidized GVAMNPVEH-PFGGGNHQHIGKPSTIR (SEQ ID NO:10) tryptic peptides from control ShRNA A549 cells. ii) LC-MS spectra of unoxidised and oxidized GVAMNPVEHPFGGGNHQHIGKP-STIR (SEQ ID NO:10) tryptic peptides from NO66 ShRNA A549 cells. C) i) LC-MS spectra of unoxidised and oxidized GVAMNPVEHPFGGGNHQHIGKPSTIR (SEQ ID NO:10) tryptic peptides from control ShRNA HeLa cells. ii) LC-MS spectra of unoxidised and oxidized GVAMNPVEH-PFGGGNHQHIGKPSTIR (SEQ ID NO:10) tryptic peptides from NO66 ShRNA HeLa cells.

BRIEF DESCRIPTION OF THE SEQUENCES

Figure 2:
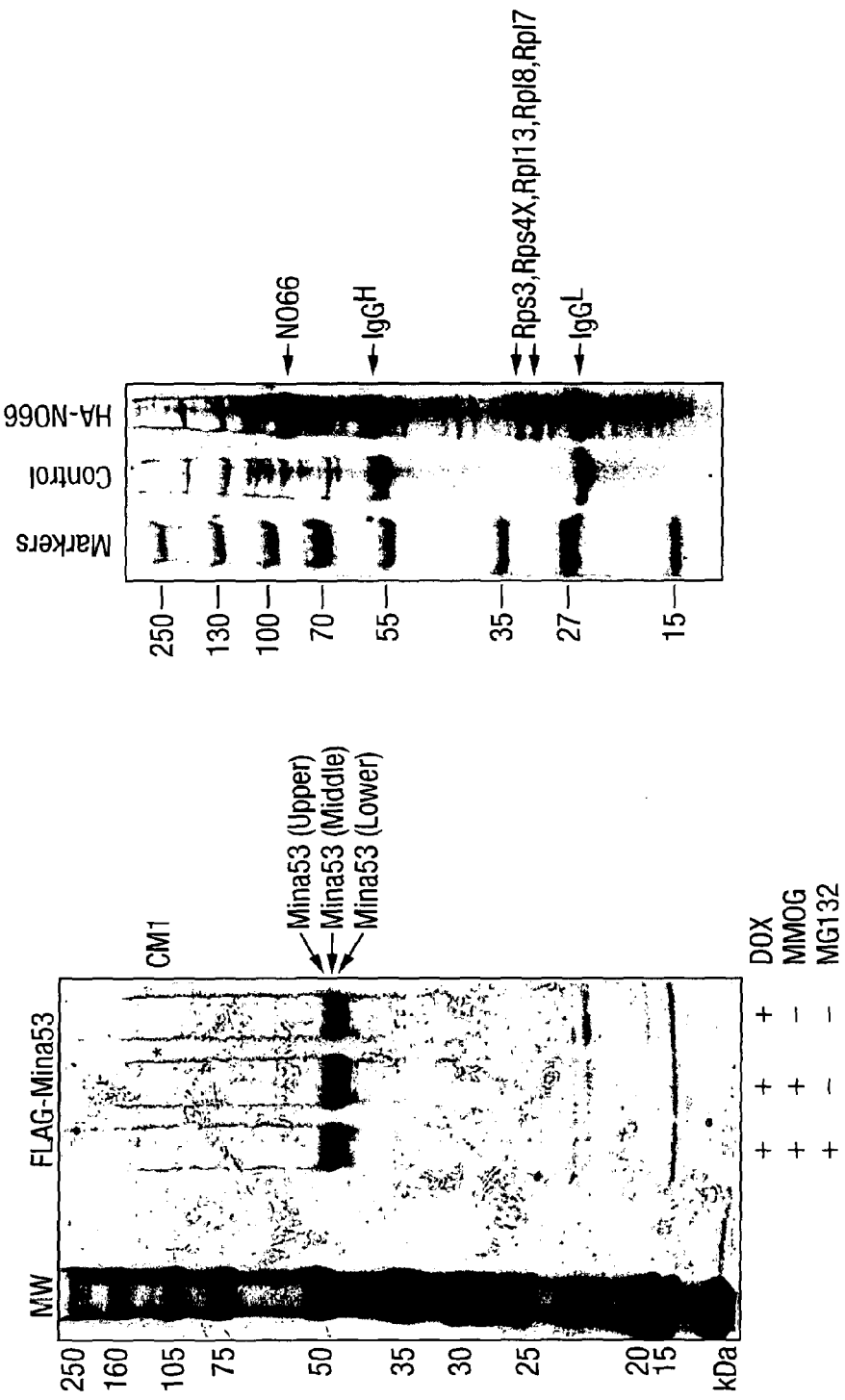
FIG. 2: Mina53 and NO66 proteomic pulldowns. A) Extracts from doxycycline-treated U2OS cells overexpressing FLAG-tagged Mina53 were immunoprecipitated with anti-FLAG antibody coupled affinity agarose. FLAG complexes were washed in lysis buffer, eluted in Laemmli buffer and separated by SDS-PAGE prior to coomassie blue staining. Co-precipitating proteins were identified by in-gel trypsinolysis and MS. B) Extracts from HEK293T cells stably overexpressing HA-tagged NO66 were immunoprecipitated with anti-HA antibody coupled affinity agarose. NO66 complexes were washed in lysis buffer, eluted in Laemmli buffer and separated by SDS-PAGE prior to coomassie blue staining. Co-precipitating proteins were identified by in-gel trypsinolysis and MS.

SEQ ID NO: 1 is the amino acid sequence of human Mina53 (gi|23307412).

SEQ ID NO: 2 is the amino acid sequence of human NO66 (gi|106879206).

SEQ ID NO: 3 is the amino acid sequence of human FIH (gi|32129605).

SEQ ID NO: 4 is the amino acid sequence of human Rpl27a (gi|4506625).

SEQ ID NO: 5 is the amino acid sequence of human Rpl8 (gi|48146209).

SEQ ID NO:6 is amino acid residues 31 to 50 of SEQ ID NO:4

SEQ ID NO:7 is amino acid residues 33 to 42 of SEQ ID NO:4

SEQ ID NO:8 is amino acid residues 209 to 228 of SEQ ID NO:5

SEQ ID NO:9 is amino acid residues 212 to 224 of SEQ ID NO:5

SEQ ID NO:10 is amino acid residues 201 to 226 of SEQ ID NO:4

SEQ ID NO:11 is amino acid residues 39 to 42 of SEQ ID NO:4

SEQ ID NO:12 is amino acid residues 215 to 218 of SEQ ID NO:5

DETAILED DESCRIPTION OF THE INVENTION

The present inventors have shown for the first time that Mina53 catalyses histidinyl-hydroxylation of the β-carbon of RpL27a His-39, and that NO66 catalyses histidinyl-hydroxylation of the β-carbon of RpL8 His-216. These activities can be inhibited by known 2OG oxygenase inhibitors. The present invention provides a method for assaying Mina53 and NO66 activities, the method comprising contacting an Mina53 and NO66 polypeptide with a peptide containing a histidinyl residue (or analogue thereof), and determining either directly or indirectly whether the peptide is hydroxylated at the histidinyl-residue.

Mina53 or NO66 polypeptides in accordance with the present invention are typically human Mina53 and NO66 or homologues thereof, variants thereof which retain histidinyl-hydroxylase activity, or a fragment of any thereof which retains histidinyl-hydroxylase activity. The sequence of human Mina53 is described in SEQ ID NO: 1. The sequence of human NO66 is described in SEQ ID NO: 2. Homologues thereof may be derived from other species, including in particular mammalian species. Exemplary species include orangutan, cow, rat and mouse.

The Mina53 polypeptide may comprise the sequence shown in SEQ ID NO: 1, or may be a fragment or variant of SEQ ID NO: 1 having histidinyl hydroxylase activity. Fragments of Mina53 are described in more detail below. The Mina53 polypeptide may have an amino acid sequence having at least about 60% sequence identity, for example at least about 70% sequence identity, with SEQ ID NO: 1 over its entire length or over an active fragment thereof, typically greater than about 80% or 90%, such as about 95% or about 99% sequence identity.

The NO66 polypeptide may comprise the sequence shown in SEQ ID NO: 2, or may be a fragment or variant of SEQ ID NO: 2 having histidinyl hydroxylase activity. Fragments of NO66 are described in more detail below. The NO66 polypeptide may have an amino acid sequence having at least about 60% sequence identity, for example at least about 70% sequence identity, with SEQ ID NO: 2 over its entire length or over an active fragment thereof, typically greater than about 80% or 90%, such as about 95% or about 99% sequence identity.

Sequence identity may be calculated using any suitable algorithm. For example, the UWGCG Package provides the BESTFIT program can be used to infer homology (for example used on its default settings) (Devereux et al. (1984) *Nucleic Acids Research* 12, p387-395). The PILEUP and BLAST algorithms can be used to infer homology or line up sequences (typically on their default settings), for example as described in Latched (1993) J. Mol. Evol 36:290-300; Latched et al. (1990) J. Mol. Biol. 215:403-10.

The Mina53 or NO66 polypeptides may be polypeptides encoded by any naturally occurring MINA53 or NO66 genes in humans or other organisms. The naturally occurring MINA53 or NO66 gene may encode the sequence shown in SEQ ID NO: 1 or NO; 2 or may encode a variant or homologue. Such variants may include allelic variants and the deletion, modification or addition of single amino acids or groups of amino acids within the protein sequence, as long as the polypeptide retains histidinyl hydroxylase activity.

Amino acid substitutions of SEQ ID NO:1 and NO:2, or fragments thereof, may be made, for example from about 1, 2 or 3 to about 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Variant polypeptides within the scope of the invention may be generated by any suitable method, for example by gene shuffling techniques.

The present invention also includes use of active portions, fragments, derivatives and functional mimetic of the polypeptides of the invention. An "active portion" of a polypeptide means a peptide which is less than said full-length polypeptide, but which retains histidinyl hydroxylase activity. An active fragment of Mina53 or NO66 may typically be identified by monitoring for 2OG oxygenase or hydroxylase activity as described in more detail below. Such an active fragment may be included as part of a fusion protein.

The Mina53 fragment may have up to about 200, 250, 300, 350, 400, 450, or 465 amino acids. The Mina53 fragment may comprise any region from the amino acid sequence shown in SEQ ID NO: 1, such as from amino acid 2, 3, 4, 5 or about 10 to about amino acid 400, 410, 420, 430, 440, 450, or 465. Useful fragments include N-terminal (or C-terminal) truncated fragments i.e., fragments comprising an N-terminal deletion, such as fragments comprising residues 10 to 465, 20 to 465 or 25 to 465 of the amino acid sequence shown in SEQ ID NO: 1. Useful fragments also include fragments comprising C-terminal truncations such as fragments comprising residues 1 to 465, 1 to 450, 1 to 440 or 1 to 430 of the amino acid sequence shown in SEQ ID NO: 1. Useful fragments also include fragments comprising both N-terminal and C-terminal truncations, such as fragment comprising residues 10 to 465, 20 to 450 or 25 to 430 of the amino acid sequence shown in SEQ ID NO: 1.

The NO66 fragment may have up to about 200, 250, 300, 350, 400, 450, 500, 550, 600, or 641 amino acids. The NO66 fragment may comprise any region from the amino acid sequence shown in SEQ ID NO: 2, such as from amino acid 2, 3, 4, 5 or about 10 to about amino acid 600, 610, 620, 630, or 641. Useful fragments include N-terminal (or C-terminal) truncated fragments i.e., fragments comprising an N-terminal deletion, such as fragments comprising residues 10 to 641, 20 to 641 or 25 to 641 of the amino acid sequence shown in SEQ ID NO: 2. Useful fragments also include fragments comprising C-terminal truncations such as fragments comprising residues 1 to 641, 1 to 630, 1 to 620 or 1 to 610 of the amino acid sequence shown in SEQ ID NO: 2. Useful fragments also include fragments comprising both N-terminal and C-terminal truncations, such as fragment comprising residues 10 to 641, 20 to 630 or 25 to 620 of the amino acid sequence shown in SEQ ID NO: 2.

Other suitable fragments of Mina53 and NO66 may readily be identified, for example by comparing the amino acid sequence to the amino acid sequence of one or more known 2OG oxygenases and identifying which regions are homologous to regions having catalytic activity. The regions having catalytic activity are typically included in the active fragments. Such fragments can be used to construct chimerical molecules. Fragments of any Mina53 or NO66 polypeptide having at least approximately 60% sequence identity (such as at least approximately 70%, 80%, 90%, 95% or 99% sequence identity to the amino acid sequence shown in SEQ ID NO: 1 or 2) that have histidinyl hydroxylase activity may also be used in an assay of the invention and are encompassed within the terms "Mina53 or NO66 polypeptides" used herein.

The Mina53 or NO66 polypeptides may comprise one or more particular site directed mutations.

The Mina53 or NO66 polypeptides may be synthetically prepared. The polypeptides may be chemically or biochemically modified, e.g. post-translationally modified. For example, they may be glycosylated or contain modified amino acid residues. They may also be modified by the addition of additional histidine residues (typically six), or other sequence tags such as a maltose binding protein tag or intein tag, to assist their purification or by the addition of a nuclear localisation sequence to promote translocation to the nucleus or mitochondria, and or by post-translational modification including hydroxylation or phosphorylation. Polypeptides of the invention may be GST or other suitable fusion polypeptides. The Mina53 or NO66 polypeptides may also be modified by addition of fluorescent tags (such as green or yellow fluorescent protein) to enable visualisation within cells or organelles or to aid purification of the protein or cells expressing Mina53 or NO66. Such modified polypeptides fall within the scope of the term "Mina53 or NO66 polypeptides".

The Mina53 or NO66 polypeptides of the invention may be present in a partially purified or in a substantially isolated form. The polypeptide may be mixed with carriers or diluents, which will not interfere with its intended use and still be regarded as substantially isolated. The polypeptide may also be in a substantially purified form, in which case it will generally comprise at least about 90%, e.g. at least about 95%, 98% or 99%, of the proteins, polynucleotides, cells or dry mass of the preparation.

The Mina53 or NO66 polypeptides used in a method of the invention may be recombinant Mina53 or NO66 or naturally occurring Mina53 or NO66. Naturally occurring Mina53 or NO66 may be obtained from any organism that produces Mina53 or NO66 polypeptides. Preferably, recombinant Mina53 or NO66 are used especially where Mina53 or NO66 is required for purposes requiring large (>20 mg) amounts of protein such as for biophysical assays or for high throughput analyses. Recombinant Mina53 or NO66 may be produced using standard expression vectors that comprise nucleotide sequences encoding Mina53 or NO66. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. (1989).

The Mina53 or NO66 polypeptides may be present in a cell, including, but not limited to, human-derived cells. For example, methods of the invention may utilise cells that have been modified to express Mina53 or NO66 polypeptides as defined herein. The Mina53 or NO66 may also be present in a cell extract or in a partially or substantially purified form.

Purified Mina53 or NO66 polypeptides may be obtained by introducing an expression vector comprising a polynucleotide encoding Mina53 or NO66 polypeptides into a host cell.

Expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art. Promoter sequences may be inducible or constitutive promoters depending on the selected assay format. The promoter may be tissue specific. Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be, for example, a plasmid, virus or baculovirus vector. The vector is typically adapted to be used in a bacterial cell, such as E. coli. The vector may have an origin of replication. The vector may comprise one or more selectable marker genes, for example an ampicillin resistance gene in the case of a bacterial plasmid or a resistance gene for a fungal vector. Vectors may be used to transfect or transform a host cell, for example, a bacterial host cell, fungal host cell, an insect host cell, a mammalian, e.g. human host cell or a baculovirus host cell.

Methods for introducing polypeptides and vectors into host cells are well known in the art, and include electroporation and heat shock techniques without limitation. Expression of the truncated polypeptide may then be achieved by culturing the host cells.

The Mina53 or NO66 polypeptides may be purified by lysing the host cells and extracting Mina53 or NO66 from the soluble fraction, for example by affinity purification, such as via an affinity tag fused to truncated Mina53 or NO66 polypeptides. Mina53 or NO66 polypeptides may be purified by standard techniques known in the art. For example, where the polypeptide comprises a His tag, it may be purified using a His-binding resin by following the manufacturer's instructions (e.g. Novagen) or by other means such as ion exchange chromatography.

The methods of the present invention typically use a peptide containing a histidinyl residue as a substrate (or binding agent) for the Mina53 or NO66 polypeptides. The general peptide's length used in the screen is typically at least 15 amino acids in length or peptide proteins, of at least 20, 40, 60, 80, 100, 120, 140, 160, 180, 200, 220, 240 or 260 amino acids in length. A full length protein which is a substrate for the Mina53 or NO66 polypeptide can be used, for example the human RpL27a (Mina53) or RpL8 (NO66) ribosomal proteins.

Any suitable peptide can be used, so long as the peptide contains a histidinyl residue (or analogue thereof) capable of hydroxylation by Mina53 or NO66 (or of binding to the active site of Mina53 or NO66). The peptide may be modified, e.g. by the presence of a group to facilitate assays such as a fluorescent group; Many such modifications are routinely used and described in the scientific literature.

In preferred aspects of the present invention, the peptide used in the assays is a substrate for Mina53 or NO66 in vivo, or a homologue, variant or fragment thereof. In particular, the present inventors have identified the ribosomal protein RpL27a to be a substrate for Mina53 and have identified the ribosomal protein RpL8 to be a substrate for NO66.

Thus, one preferred Rpl27a derived peptide (GRGNAGGLHHHRINFDKYHP) (SEQ ID NO:6) containing a histidinyl residue for use in accordance with the present invention is a fragment of SEQ ID NO: 4. One preferred Rpl8 derived peptide (HPFGGGNHQHIGKPSTIRRD) (SEQ ID NO:8) containing a histidinyl residue for use in accordance with the present invention is a fragment of SEQ ID NO: 5.

Sequence identity may be calculated using any suitable algorithm. For example, the UWGCG Package provides the BESTFIT program can be used to infer homology (for example used on its default settings) (Devereux et al. (1984) Nucleic Acids Research 12, p387-395). The PILEUP and BLAST algorithms can be used to infer homology or line up sequences (typically on their default settings), for example as described in Latched (1993) J. Mol. Evol 36:290-300; Latched et al. (1990) J. Mol. Biol. 215:403-10.

Amino acid substitutions of SEQ ID NO: 4 and 5, or of fragments thereof, may be made, for example from about 1, 2 or 3 to about 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Mina53 Substrate

Mina53 has been showed to hydroxylate the histidinyl residue at position H39 of RpL27a SEQ ID NO: 4. Thus a variant or homologue of SEQ ID NO: 4 includes a residue equivalent to histidinyl residue at position H39 of SEQ ID NO: 4.

The assays of the present invention also include the use of fragments of SEQ ID NO: 4 or fragments of the variants thereof as defined above. Such fragments may be as short as 6 amino acids in length, typically at least 10, 11, 12 or 13 or 14 amino acids in length, preferably 16, 17, 18, 19 or 20 amino acids in length and incorporate an histidinyl equivalent to histidine at position H39 of SEQ ID NO: 4. The peptide typically comprises the sequence HHHR1 (SEQ ID NO:11). A preferred fragment of RpL27a is GRGNAGGLHHHRINFDKYHP (SEQ ID NO:6) corresponding to residues 31 to 50 of SEQ ID NO: 4. In a preferred embodiment, a peptide substrate for use in accordance with the present invention consists of or comprises this sequence, or variants thereof having 1, 2 or 3 substitutions therein, and retaining a histidine residue (or analogue thereof) equivalent to His 39 of SEQ ID NO: 4.

NO66 Substrate

NO66 has been showed to hydroxylate the histidinyl residue at position H216 of Rpl8 SEQ ID NO: 5. Thus a variant or homologue of SEQ ID NO: 5 includes a histidinyl residue (or analogue thereof) equivalent to the histidinyl residue at position 216 of SEQ ID NO: 5.

The assays of the present invention also include the use of fragments of SEQ ID NO: 5 or fragments of the variants thereof as defined above. Such fragments may be as short as 6 amino acids in length, typically at least 10, 11, 12 or 13 or 14 amino acids in length, preferably 16, 17, 18, 19 or 20 amino acids in length and incorporate an histidinyl equivalent to histidine at position 216 of SEQ ID NO: 5. The peptide typically contains the sequence NHQH. A preferred fragment of Rpl8 is HPFGGGNHQHIGKPSTIRRD (SEQ ID NO:8), residues 209 to 228 of SEQ ID NO: 5. In a preferred embodiment, a peptide substrate for use in accordance with the present invention consists of or comprises this sequence, or variants thereof having 1, 2 or 3 substitutions therein, and retaining a histidine equivalent to His 216 of SEQ ID NO: 5.

The method of the invention may be used to identify modulators of Mina53 or NO66 activity. The assay may be carried out in the presence of a test agent to determine whether the test agent is a modulator of Mina53 or NO66 activity. Such assays may use purified materials or be carried out in cells. Any suitable assay may be carried out to identify modulators of Mina53 or NO66 histidinyl hydroxylase activity. A number of different examples of suitable assays are described below. Assays of the invention may be used to identify an agent which modulates, such as inhibits or activates, Mina53 or NO66 histidinyl hydroxylase activity.

In a method of the invention Mina53 or NO66 histidinyl hydroxylase activity may be assayed by monitoring oxygenase activity of Mina53 or NO66 polypeptides in the presence of substrate. In some embodiments, the substrate is a ribosomal protein such as the human ribosomal protein RpL27a (or other Mina53 substrate containing a histidinyl-residue) or the human ribosomal protein RpL8 (or other NO66 substrate containing a histidinyl-residue). In some embodiments, the Mina53 polypeptide hydroxylates His-39 of the ribosomal protein RpL27a, or fragment or analogue thereof. In some embodiments, the NO66 polypeptide hydroxylates His-216 of the ribosomal protein Rpl8, or fragment or analogue thereof. The substrate and the Mina53 or NO66 polypeptides, and optionally the test agent, are typically contacted under conditions suitable for oxygenase (hydroxylase) activity.

Suitable co-substrates include oxygen, for example, dioxygen, and 2-oxoacids such as 2-oxoglutarate (2OG) or 2OG analogues (such as 2-oxoadipate). Preferably, the co-substrate is 2OG. In addition to oxygen or a 2-oxoacid, a reducing agent, such as ascorbate may also be used as a cofactor. Thus, in a method according to the invention, the ribosomal protein or analogue or fragment thereof and Mina53 or NO66 polypeptides are contacted in the presence of Fe(II), oxygen and 2-oxoglutarate and optionally in the presence of a reducing agent.

Hydroxylation of the substrate may be assayed directly or indirectly. Such assays may employ techniques such as chromatography, NMR, MS or fluorescence spectroscopy. The co-substrate may be modified, e.g. 2OG, consumed, e.g. oxygen, or produced, e.g. succinate or carbon dioxide, by Mina53 or NO66 polypeptides.

In an assay to identify a modulator of Mina53 or NO66 activity, the components of the assay are preferentially contacted under conditions in which Mina53 or NO66 have histidinyl hydroxylase/oxygenase activity both in the absence of the test agent and in the presence of the test agent so that the effect of the test agent on Mina53 or NO66 activity may be determined. The assay may also be used to detect agents that increase or decrease the activity of Mina53 or NO66 activity by assaying for increases or decreases in activity including in while organisms. Suitable assays have been described in the art for other 2OG oxygenases including the HIF hydroxylases and histone demethylases. Other assay configurations may rely on methods for assessing binding, e.g. by displacement of an appropriately labelled Mina53 or NO66 binding peptide from the Mina53 or NO66 active site. Cell-based assays in which the hydroxylation status of RpL27a or RpL8 are assessed either by mass spectrometry or by use of appropriate antibodies are also suitable. Such assays have been developed for the HIF prolyl hydroxylases and OGFOD1 and are amenable to the study of Mina53 or NO66 activity in animals including humans, and in different tissue types (healthy and diseased). Measurement of Mina53 or NO66 activity is of particular interest with respect to investigating the hydroxylation status of ribosomes in tissues that are subject to diseases associated with hypoxia such as many tumours, and indeed altered ribosome hydroxylation may be characteristic of such diseases.

Assays of the present invention may be used to identify inhibitors of oxygenase activity and are thus preferably, but not necessarily, carried out under conditions under which Mina53 or NO66 are active as an oxygenase (a histidinyl hydroxylase) in the absence of the test agent. The Mina53 or NO66 oxygenase activity in the presence of the test agent is compared to Mina53 or NO66 oxygenase activity in the absence of the test substance to determine whether the test substance is an inhibitor of Mina53 or NO66 oxygenase activity. In the alternative, the assays may be used to look for promoters of Mina53 or NO66 oxygenase activity, for example, by looking for increased conversion of co-substrate and/or hydroxylation of substrates compared to assays carried out in the absence of a test substance. The assays may also be carried out, either with purified materials in cells or in animals, under conditions in which Mina53 or NO66 oxygenase activity is reduced or absent, such as under hypoxic conditions, and the presence of or increased activity can be monitored under such conditions.

In medicinal applications, for example, it is often advantageous to modulate oxygenase activity of a single enzyme or group of enzymes. The assays of the invention may also be used to identify inhibitors or activators that are specific for histidinyl hydroxylases, such as Mina53 and/or NO66 (or homologues of Mina53 or NO66) and which do not have activity or are less active with other 2OG oxygenases, including other human 2OG oxygenases, for which assays have been reported or which are amenable to reported assays for 2OG oxygenases. Conversely, the assays of the invention may be used to identify inhibitors or activators specific for one or more 2OG oxygenases which do not inhibit Mina53 OR NO66 activity. Human 2OG oxygenases that may be tested in such a method of the invention include, but are not limited to: argininyl, prolyl, and asparaginyl demethylases, hypoxia inducible factor (HIF) asparaginyl or prolyl hydroxylases, including FIH, PHD1, PHD2 and PHD3, and nucleic acids modifying enzymes including ABH1, ABH2, ABH3 and ABH8, procollagen prolyl and lysyl hydroxylases, methyl arginine demethylases, the fat mass and obesity protein, the epidermal growth factor hydroxylases, AlkB, TauD, and other 2OG oxygenases that have been characterized as JmjC domain proteins according to the SMART database including, but not limited to argininyl demethylases.

The present invention also provides a method for identifying a selective inhibitor of Mina53 or NO66 (or Mina53 or NO66 homologue), or an inhibitor that is selective for another 2OG oxygenase over Mina53 or NO66. This method comprises: (i) contacting an Mina53 or NO66 substrate, such as Rpl27a and Rpl8 respectively, or fragment thereof comprising a histidinyl residue, with an Mina53 or NO66 polypeptide in the presence of a test agent and determining whether the protein or fragment thereof is hydroxylated; (ii) determining whether the test agent modulates activity of a 2OG oxygenase other than Mina53 or NO66, thereby determining whether the test agent selectively modulates Mina53 or NO66 activity or selectively modulates activity of the 2OG oxygenase other than Mina53 or NO66. Many inhibitors of 2OG oxygenases have been reported and well-established medicinal chemistry techniques can be used to develop and select inhibitors of specific enzyme or group of enzymes.

Oxygenase activity of the 2OG oxygenase other than Mina53 or NO66 may be determined by contacting a substrate of the 2OG oxygenase with the 2OG oxygenase in the presence of a test agent and determining whether the substrate is hydroxylated or demethylated or otherwise oxidized. In an assay to identify a selective inhibitor of Mina53 or NO66, or another oxygenase, different substrates may be used for Mina53 or NO66 and for the other oxygenase(s).

Alternatively, oxygenase activity of the 2OG oxygenase other than Mina53 or NO66 may be determined in the absence of a prime substrate (i.e., a non-2OG substrate). This enables selective inhibitors to be identified when the prime substrate of one or more of the enzymes being tested is unknown. In this embodiment, generally it will be one or more of the enzymes that it is wished not to inhibit that is an enzyme that has an unknown substrate. The effect of a test agent on activity of an oxygenase may be determined in the absence of a substrate by determining whether or not the test agent affects, for example inhibits or stimulates, the rate of turnover of 2OG by the oxygenase.

Thus, the invention also provides methods for screening for compounds that do not inhibit Mina53 or NO66. Such compounds are of use with respect to developing inhibitors that are selective for 2OG oxygenases other than Mina53 or NO66. Mina53 or NO66 inhibitors that do not inhibit the HIF prolyl or asparaginyl hydroxylases are of interest. Standard methods can be used to develop selective inhibitors including examples of developing selective 2OG oxygenase inhibitors, for example, for the HIF prolyl hydroxylases over the HIF asparaginyl hydroxylase. The development of selective inhibitors may employ structural methods that identify differences in the active sites between the enzymes of interest (e.g. between Mina53 or NO66 and the HIF prolyl hydroxylases and or the human collagen prolyl hydroxylases).

The assays of the invention may also be used to identify inhibitors or activators, which are specific for Mina53 or NO66 activity at a particular substrate or residue within a substrate.

Such selectivity screens may be used to identify selective inhibitors of Mina53 or NO66 or selective inhibitors of other enzymes, i.e. inhibitors that are more potent inhibitors of Mina53 or NO66 activity than of activity of the other enzyme or inhibitors that are less potent inhibitors of Mina53 or NO66 activity than of activity of the other enzyme. Where the inhibitor is a selective inhibitor of Mina53 or NO66 activity it may have no effect on the activity of the other enzyme or may exhibit only a low level of inhibition, such as less than about 50% inhibition on activity of the other enzyme. Where the inhibitor is a selective inhibitor of the activity of the enzyme other than Mina53 or NO66, it may have no effect on the activity of Mina53 or NO66 or may exhibit only a low level of inhibition, such as less than about 50% inhibition of Mina53 or NO66 activity.

The selectivity screens may be carried out with purified enzymes, partially purified enzymes (such as in crude cell lysates) or in cells, or in animals including humans, and employ the assays methods listed above or other methods.

The invention provides for the use of selective inhibitors in the manufacture of a medicament for the treatment of a condition associated with altered, i.e. enhanced or reduced Mina53 or NO66 oxygenase activity.

The precise format of any of the assay or screening methods of the present invention may be varied by those of skill in the art using routine skill and knowledge. The skilled person is well aware of the need to additionally employ appropriate controlled experiments. The assays of the present invention may involve monitoring for hydroxylation of the substrate, monitoring for the utilisation of substrates and co-substrates, monitoring for the production of the expected products between the enzyme and its substrate. Assay methods of the present invention may also involve screening for the direct interaction between components in the system. Alternatively, assays may be carried out which monitor for downstream effects mediated by the substrate, such as substrate mediated transcription using suitable reporter constructs or by monitoring for the upregulation of genes or alterations in the expression patterns of genes known to be regulated directly or indirectly by the substrate.

Various methods for determining oxygenase activity either directly or indirectly are known in the art. Any suitable method may be used for determining 2OG oxygenase activity of Mina53 or NO66 such as by substrate or co-substrate utilisation, product appearance such as peptide hydroxylation (or demethylation for some 2OG oxygenases) or downstream effects mediated by hydroxylated products (or demethylated or non-hydroxylated products for some 2OG oxygenases).

The substrate, enzyme and potential inhibitor compound may be incubated together under conditions which, in the absence of inhibitor provide for hydroxylation (or demethylation for some 2OG oxygenases) of the substrate, and the effect of the inhibitor may be determined by determining hydroxylation (or demethylation for some 2OG oxygenases) of the substrate. This may be accomplished by any suitable means. Small polypeptide or polynucleotide substrates may be recovered and subjected to physical analysis, such as mass spectrometry, radiography or chromatography, or to functional analysis. Such methods are known as such in the art and may be practiced using routine skill and knowledge. Determination may be quantitative or qualitative. In both cases, but particularly in the latter, qualitative determination may be carried out in comparison to a suitable control, e.g. a substrate incubated without the potential inhibitor.

In alternative embodiments, reporter constructs may be provided in which promoters mediated by a substrate are provided operably linked to a reporter gene. Any suitable reporter gene could be used, such as for example enzymes which may then be used in colorimetric, fluorimetric, fluorescence resonance or spectrometric assays.

In the assay methods described herein, typically the Mina53 or NO66 polypeptide and the substrate are contacted in the presence of a co-substrate, such as oxygen and/or a 2-oxoacid, such as 2OG (or analogue thereof). Hydroxylase activity may be determined by determining turnover of one or more of the co-substrates, such as oxygen or 2OG. This may be achieved by determining the presence and/or amount of reaction products, such as hydroxylated substrate, carbon dioxide or succinic acid. The amount of product may be determined relative to the amount of substrate. For example, in such embodiments the product measured may be hydroxylated peptide or protein. In the case of protein the extent of hydroxylation may also be determined in cells, e.g. by the use of appropriate antibodies or by mass spectrometry. For example, the extent of hydroxylation may be determined by measuring the amount of hydroxylated peptide/protein, succinate, carbon dioxide, or formaldehyde generated in the reaction, or by measuring the depletion of 2OG or dioxygen. Methods for monitoring each of these are known in the scientific literature, for example in Myllyharju et al. (1991) EMBO J. 16(6): 1173-1180 or as in Cunliffe et al. (1986) Biochem. J. 240: 617-619. An assay that measures oxygen consumption such as that described by Ehrismann et al. Biochem J. (2007) may be used. In addition, an enzyme activity assay that measures $^{14}CO_2$ generated from the decarboxylation of $[^{14}C]$-2OG coupled to hydroxylation (Kivirikko K I, Myllyla R. Methods Enzymol (1982) may also be used. (Dissolved oxygen electrodes, exemplified by but not limited to a "Clarke-type" electrode or an electrode that uses fluorescence quenching, may be used to follow the consumption of oxygen in an assay mixture.) Use of ion-exchange chromatography to separate $[^{14}C]$-succinic acid and $[5-^{14}C]$-2OG or separation using 2,4-dinitrophenylhydrazine to precipitate $[5-^{14}C]$-2OG may also be used. Measuring conversion of $[5-^{14}C]$-2OG to $[^{14}C]$-succinic acid, Kanelakis K C, Palomino H L, Li L, et al. J Biomol Screen (2009), may also be used. The formation of a hydroxylated peptide fragment can be determined directly, e.g. by using either LC/MS analysis, Li D, Hirsila M, Koivunen P, et al. J Biol Chem (2004), or matrix-assisted laser desorption ionization, time-of-flight mass spectrometer or by other assay monitoring hydroxylation. Monitoring the consumption of a reducing agent such as potassium ferrocyanide (replacing ascorbate) FibroGen, Inc. WO2005118836; 2007 may be used. Antibody based methods may also be used by employing an antibody selective for a hydroxylated product or non-hydroxylated substrate. Antibody based methods may be enhanced such that they are more efficient for modulator screening, e.g. by use of homogenous time resolved fluorescence (HTRF) methods which measure the energy transfer between a labelled dye (e.g., via biotin-streptavidin complex) to hydroxyl-proline peptide fragment substrate, and europium, which is tagged to a hydroxyl-proline specific antibody similar to methods described in Dao J H, Kurzeja R J M, Morachis J M, et al. Anal Biochem (2009). Assays that measure displacement of a substrate from Mina53 or NO66 may also be employed—these may employ the use of suitably tagged reagents and antibodies.

The amount of unused 2OG may be determined, e.g., by spectroscopy or derivatisation by chemical reagents, exemplified by but not limited to hydrazine derivatives and orthophenylene diamine derivatives, to give indicative chromophores or fluorophores that can be quantified and used to indicate the extent of hydroxylation of the substrate. Suitable methods are described in McNeill et al. (2005) (Anal. Biochem. 366:125-131). The fluorescent product of the reaction of ortho-phenylenediamine (OPD) with the α-ketoacid motif of 2OG is 3-(2-carboxyethyl)-2(1H)-quinoxalinone. This fluorescent product can be readily detected by standard equipment such as that manufactured by for example Molecular Devices, Tecan, BMG Labtechnologies, Jasco and Perkin Elmer and there is extensive precedent demonstrating that the production of fluorescent products can be used in high-throughput screens.

The precise format of any of the screening or assay methods of the present invention may be varied by those of skill in the art using routine skill and knowledge. The skilled person is well aware of the need to additionally employ appropriate control experiments.

Other components may be added to the assay mixtures. For example, a reducing agent such as ascorbate, a thiol such as dithiothreitol (DDT), β-mercaptoethanol, tris(2-carboxyethyl)phosphine hydrochloride (TCEP), N-acetylcysteine or phenol may be added to the assay to help maintain enzyme structure and/or catalase may be added to destroy any $H_2O_2$ that might be produced. However, the assay will work in the absence of a reducing agent or catalase.

Assays are typically carried out at a temperature of from about 25° C. to about 40° C., for example at a temperature of from about 30° C. to about 39° C., or from about 35° C. to about 38° C. or about 37° C. The pH of the assay mixture is typically between about pH 7 to about pH 9, for example from about pH 7.5 to about pH 8. Suitable buffers, such as Tris or HEPES, may be used to maintain the pH of the assay mixture.

Typically, assays are carried out under normoxic conditions, but may be carried out at oxygen concentrations above or below atmospheric levels. The assay may also be carried out under conditions in which hydroxylation or oxidation is reduced or absent, such as under hypoxic conditions, in order to detect modulation of oxygenase activity by an agent which enhances hydroxylation/oxidation.

Alternatively, the end-point determination may be based on conversion of the substrate or substrate fragments (including synthetic and recombinant peptides or nucleic acids) derived from the polypeptide or nucleic acid substrate into detectable products. Substrates may be modified to facilitate the assays so that they can be rapidly carried out and may be suitable for high throughput screening.

For example, reverse phase HPLC (C-4 octadecylsilane column), as exemplified herein, may be used to separate starting synthetic peptide substrates from the products. Modifications of this assay or alternative assays for oxygenase activity may employ, for example, mass spectrometric, spectroscopic, and/or fluorescence techniques as are well known in the art (Masimirembwa C. et al. Combinatorial Chemistry & High Throughput Screening (2001) 4 (3) 245-263, Owicki J. (2000) J. Biomol. Screen. 5 (5) 297-305, Gershkovich A et al. (1996) J. Biochem. & Biophys. Meths. 33 (3) 135-162, Kraaft G. et al. (1994) Meths. Enzymol. 241 70-86). Fluorescent techniques may employ versions of the substrate modified in such as way as to carry out or optimise spectroscopic or fluorescence assays.

Binding of a molecule, such as an antibody, which discriminates between the hydroxylated and non-hydroxylated forms of a peptide or protein may be assessed using any technique available to those skilled in the art, which may involve determination of the presence of a suitable label.

Assay methods of the present invention may also take the form of an in vivo assay or an assay carried out on ex vivo cells from an animal, such as a mammal (including human) or an insect. The assay may be performed in a cell line such as a yeast or bacterial strain or an insect or mammalian cell line in which the relevant polypeptides or peptides are expressed endogenously or from one or more vectors introduced into the cell. Such assays may employ the use of antibodies specific for hydroxylated or non-hydroxylated forms of Mina53 or NO66 substrates, or may employ proteomic mass spectrometry-based methods based on protease-catalysed digestions or analyses on intact proteins.

The invention further provides a method for identifying a modulator of protein production, the method comprising contacting a cell (a organism) which expresses Mina53 or NO66 with a test agent and determining whether the test agent modulates Mina53 or NO66 regulation of protein translation.

The invention further provides a method for distinguishing between cells that are hypoxic and normoxic. This is because the Mina53 and NO66 activities are dependent on oxygen.

Thus, the degree of hydroxylation of Mina53 or NO66 substrates, e.g. RpL27a or RpL8, is dependent on oxygen availability and the extent of hydroxylation will refect oxygen availability. The invention thus further discloses a way of selectively targeting hypoxic cells (such as cancer cells) by use of compounds that preferably inhibit ribosomes that are hydroxylated by Mina53/NO66, or which are not hydroxylated as a result of impaired Mina53 or NO66 activity (i.e. translation). Many ribosome inhibitors are available and some are used as antibiotics and some possess anti-tumor activity. Modification at there, or other inhibitors, will able selective recognizing a hydroxylated or non-hydroxylated ribosomes.

In one embodiment Mina53 or NO66 may be over-expressed in cells. Mina53 or NO66 may be over-expressed in a cell in vitro or in vivo by any suitable method, typically by introducing an expression vector encoding a Mina53 or NO66 polypeptide into the cell. Protein translation (or translation accuracy) may be monitored in the cell over-expressing Mina53 or NO66 and compared to protein translation in a control cell that does not over-express Mina53 or NO66. The cell over-expressing Mina53 or NO66 may be contacted with a test agent and protein translation may be monitored in the presence of the test agent. By comparing translation observed in the presence and absence of the test agent and in the presence and absence of Mina53 or NO66 over-expression, it may determine whether the test agent modulates Mina53 or NO66-mediated regulation of protein translation. Levels of Mina53 or NO66 catalysed hydroxylation in cells may be determined by use of antibodies or by mass spectrometric methods as routinely used in proteomic analyses.

In another embodiment, Mina53 or NO66 may be underexpressed in cells. Mina53 or NO66 may be under-expressed in cells in vitro or in vivo by any suitable method, for example by using RNAi/ShRNA technology to knock down the Mina53 or NO66 protein. Protein translation may be monitored in the cell under-expressing Mina53 or NO66 and compared to protein translation in a control cell that does not under-express Mina53 or NO66. The cell under-expressing Mina53 or NO66 may be contacted with a test agent and protein translation may be monitored in the presence of the test agent. By comparing the protein translation observed in the presence and absence of the test agent and in the presence and absence of Mina53 or NO66 under-expression, it may be determined whether the test agent modulates Mina53 or NO66-mediated regulation of protein translation.

Methods for monitoring protein translation rate and or translation accuracy are well known in the art. For example, protein translation may be monitored using a reporter construct. Thus, in a method for identifying a modulator of protein translation according to the invention, the cell may comprise a protein translation reporter construct and the method may comprise determining whether Mina53 or NO66-mediated regulation of protein translation of the reporter construct is modulated by the test agent.

Agents, which may be screened using the assay methods described herein, may be natural or synthetic chemical compounds used in drug screening programmes. Extracts of plants, microbes or other organisms, which contain several, characterised or uncharacterised components may also be used.

Combinatorial synthesis technology (including solid phase synthesis and parallel synthesis methodologies) can provide an efficient way of testing a potentially vast number of different substances for ability to modulate an interaction. Such libraries and their use are known in the art, for all manner of natural products, small molecules and peptides, among others. The use of peptide libraries may be preferred in certain circumstances. Various commercial libraries of compounds are also available. There are computational methods for screening these libraries (processes sometimes referred to as virtual screening) that can identify lead structures for inhibition.

Potential inhibitor compounds (i.e. antagonists) may be polypeptides, peptides, small molecules such as molecules from commercially available libraries, including combinatorial libraries, or the like. The peptide may be a cyclic peptide and may contain non proteinogenic residues. Small molecule compounds, which may be used, include 2OG analogues, or substrate analogues, which inhibit the action of the enzyme. Small molecule compounds, and other types of compound, that may be used include all known 2OG oxygenase inhibitors such as those already known to inhibit HIF hydroxylases (see for example WO03/080566, WO02/074981, WO2007/146483, WO2007136990, WO2007/103905, WO2007/150011, US2007/0299086, US2007/0249605 and US2007/0213335), procollagen prolyl hydroxylases, and histone demethylases (for which the output of high throughput screening data is publicly available—see e.g. King et al. PLoS ONE 5(11): e15535. doi:10.1371/journal.pone.0015535 and associated material).

Potential promoting agents may be screened from a wide variety of sources, particularly from libraries of small compounds, which may be commercially available. Candidate compounds to be screened, may include 2OG analogues, compounds that chelate iron or known families of 2OG oxygenases inhibitors.

Since naturally occurring compounds, including TCA cycle intermediates such as fumarate and succinate, are known inhibitors of 2OG oxygenases they may inhibit MINA53 or NO66 possibly in a manner that is of physiological relevance, including in some cancers where fumarate is known to be upregulated.

A test compound which increases, potentiates, stimulates, disrupts, reduces, interferes with or wholly or partially abolishes hydroxylation of the substrate and which may thereby modulate activity, may be identified and/or obtained using the assay methods described herein.

Agents which increase or potentiate hydroxylation (i.e. agonists), may be identified and/or obtained under conditions which, in the absence of a positively-testing agent, limit or prevent hydroxylation. Such agents may be used to potentiate, increase, enhance or stimulate the oxygenase activity of Mina53 or NO66.

In various aspects, the present invention provides an agent or compound identified by a screening method of the invention to be a modulator of MINA53 or NO66 oxygenase activity e.g. a substance which inhibits or reduces, increases or potentiates the activity of Mina53 or NO66.

The test agent may compete with 2OG or an Mina53 or NO66 substrate at the Mina53 or NO66 active site and/or binds to the active site of Mina53 or NO66 or to metal at the Mina53 or NO66 active site. The test agent may comprise a metal ion such as, but not limited to, manganese, cobalt, zinc or nickel ions as inhibitors or iron (II), iron (III) as activators. Alternatively, the mode of inhibition may be via competition with the substrate or by an allosteric interaction.

The test agent may be a reducing agent. Reducing agents typically act as activators of 2OG oxygenase activity, typically in vitro. An activator of oxygenase activity may be any species that increases oxygenase activity of a Mina53 or NO66 polypeptide either in vitro or in vivo. Reducing agents that may be used include ascorbate and analogues of ascorbate and reducing agents of the thiol chemical families, such as dithiothreitol or phosphine (e.g. triscarboxyethylphosphine).

Following identification of a modulator, the substance may be purified and/or investigated further (e.g. modified) and/or manufactured. A modulator may be used to obtain peptidyl or non-peptidyl mimetics, e.g. by methods well known to those skilled in the art and discussed herein. A modulator may be modified, for example to increase selectively, as described herein. It may be used in a therapeutic context as discussed below.

For therapeutic treatment, the modulator may be alone or used in combination with any other therapeutically active substance or treatment including but not limited to metal ions or succinate or fumarate (Chen et al. J Biol Chem 2010).

The compounds which are acids can be present in the form of salts, such as sodium salts. The compounds may also be present in the form of derivatives such as a dimethyl ester, diethyl ester, monoethyl ester or di- or mono-amide, or other prodrug form rendering suitable pharmacokinetic properties. In certain instances these derivatives may be preferred, for example when inhibition of the enzyme within a cell of an organism is required.

Compounds which modulate 2OG oxygenases may be useful as agents of the invention, for example, in the treatment of disorders as described herein, or may be used as test substances in an assay of the invention. The test compound may be known to act as an inhibitor of a 2OG oxygenase other than Mina53 or NO66. For example, the test agent may be a described inhibitor of procollagen prolyl hydroxylase, hypoxia inducible factor, prolyl and asparaginyl hydroxylases, collagen prolyl hydroxylase, gibberellin C-20 oxidase, a nucleic acid demethylase such as AlkB or a human AlkB homologue, a protein demethylase, such as a tri-, di-, monomethyl lysine or arginine residue demethylase, another human or animal 2OG oxygenase involved in metabolism or regulation, or a plant 2OG hydroxylase. Many inhibitors of 2OG oxygenases are known in particular for human prolyl hydroxylases and histone demethylases. N-Oxalylglycine and its derivatives are such examples, but there are many others, which one of skilled in the art of oxygenases may test as Mina53 or NO66 inhibitors, glycine or alanine derivatives and 2-oxoacid analogues may also be used.

Compounds which modulate 2OG oxygenases, and families of such compounds, are known in the art, for example in Aoyagi et al. (2002) Hepatology Research 23 (1): 1-6, Aoyagi et al. (2003) Free Radical Biology and Medicine 35:410 Suppl. 1, Philipp et al. (2002) Circulation 106 (19): 1344 Suppl. S, Ivan et al. (2002) PNAS USA 99 (21): 13459-13464, Nwogu et al. (2001) Circulation 104 (18): 2216-2221, Myllyharju and Kivirikko (2001) Ann Med 33 (1): 7-21, Ohta et al. (1984) Chemical and Pharm Bulletin 32 (11): 4350-4359, Franklin et al. (2001) Biochem J. 353: 333-338, Franklin (1997) Int J. Biochem Cell Biol 29 (1): 79-89, Dowell et al. (1993) Eur J Med Chem 28 (6): 513-516, Baader et al. (1994) Biochem. J. 300: 525-530, Baader et al. (1994) Eur J Clin Chem and Clin Biol 32 (7): 515-520, Bickel et al. (1998) Hepatology 28 (2): 404-411, Bickel et al. (1991) J. Hepatology 13: S26-S34 Suppl. 3, U.S. Pat. No. 6,200,974, U.S. Pat. No. 5,916,898, US Patent Applications 2003-0176317, 2003-0153503 and 2004-0053977, WO 02/074981, WO 03/080566, WO 04/035812, Cunliffe et al. (1992) J. Med. Chem. 35:2652-2658, Higashide et al. (1995) J. Antibiotics 38:285-295, Cunliffe et al. (1986) Biochem. J. 239(2):311-315, Franklin et al. (1989) Biochem. J. 261(1):127-130, Friedman et al. (2000) PNAS USA 97(9):4736-4741, Wu et al. (1999) J. Am. Chem. Soc. 121(3): 587-588, DE-A-3818850, Wang et al. (2001) Biochemistry US:15676-15683 and Lerner et al. (2001) Angew Chem. Int. Edit. 40:4040-4041. Rose et al. J Med Chem (2008), Rose et al. J Med Chem (2010), Conjeo-Garcia et al. Bioorg Med Chem Lett. (2010), Banjeri et al. Chem Commun (2005), Hewitson et al. J Biol Chem (2007), McDonough et al. J Am Chem Soc (2005), Mecinovic et al. Bioorg Med Chem Lett (2009), Lienard et al. Chem Commun (2008), Hamada et al. J Med Chem (2010), Simkhovich et at Biochem Pharmacol (1988).

Suitable compounds are disclosed in WO03/080566, WO02/074981, WO2007/146483, WO2007136990, WO2007/103905, WO2007/150011, US2007/0299086, US2007/0249605, WO2009/074498 and US2007/0213335. Other suitable compounds include inhibitors of HIF hydroxylase. HIF hydroxylase inhibitors are disclosed in United States Patent Application Publication Nos: 20070042937, 20060276477, 20060270699, 20060258702, 20060258660, 20060251638, 20060183695, 20060178317 and 20060178316 and in International Patent Application Publication Nos: WO2007/070359, WO2008/002576, WO2007/103905, WO2005118836, WO2003049686, WO2003053997, US20060276477, US20070292433, US20070293575, WO2004108121. US20060251638, WO2004052285, WO2005011696, WO2005034929, WO2004052284, WO2006099610, WO2007097929, WO2009075824, WO2009075826, WO2006138511, WO2009058403, WO2009075826, WO2006138511, WO2009058403, WO9921860, WO2006094292, WO2007090068, WO2007115315, WO2009073669, WO2009089547, WO2009100250, WO2010056767, WO2010022240, WO2004052313, WO2007038571, WO2007103905, WO2007136990, WO2009039323, WO2009039321, WO2009039322, WO2010022307, WO2009070644, WO2009073497, WO2009134850, WO2009134847, WO2007150011, US20080171756, WO2008089052, WO2009158315, WO2010025087, WO2009049112, WO2009086044, WO2010022308, WO2010059549, WO2010059552, WO2010059555, WO2007070359, WO2008076425, WO2008137084, WO2008076427, WO2008130508, WO2008130600, WO2008137060, WO2006114213, WO2008067874, DE102007044032, WO2008049538, DE102007048447, DE102007049157, WO2008067871, US20090269420, WO2008130527, WO2009108496, WO2009108497, WO2009108499, WO2008144266, WO2009137291, WO2009117269, WO2009134750, WO2009134754, US20080124740, US20070299086, WO2009037570, WO2010018458, WO2009016812.

The present invention provides the use of an inhibitor or activator of 2OG oxygenase activity to modulate histidinyl hydroxylation of ribosomal proteins by Mina53 or NO66.

A compound, substance or agent which is found to have the ability to affect the oxygenase (histidinyl hydroxylase) activity of Mina53 or NO66 has therapeutic and other potential uses in a number of contexts, as discussed.

The modulator of Mina53 or NO66 histidinyl hydroxylase activity, may be a known inhibitor of a 2OG oxygenase, such as an N-oxalyl amino acid such as N-oxalylglycine (NOG) or a derivative thereof, a glycine or alanine derivative, a 2-oxoacid analogue, a bipyridyl derivative, a diacylhydrazine, a catechol or catechol derivative such as gallic acid, or pyridine-2,4-dicarboxylic acid or FG2216. The inhibitor may be a selective inhibitor of Mina53 or NO66 activity compared to other 2OG oxygenases.

An agent identified using one or more primary screens (e.g. in a cell-free system) as having ability to modulate oxygenase activity may be assessed further using one or more secondary screens.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent.

The invention further provides compounds obtained by assay methods of the present invention, and compositions comprising said compounds, such as pharmaceutical compositions wherein the compound is in a mixture with a pharmaceutically acceptable carrier or diluent. Examples of suitable carriers or diluents are given in, for example, "Harrison's Principles of Internal Medicine". The carrier may be liquid, e.g. saline, ethanol, glycerol and mixtures thereof, or solid, e.g. in the form of a tablet, or in a semi-solid form such as a gel formulated as a depot formulation or in a transdermally administrable vehicle, such as a transdermal patch.

The invention further provides a method of treatment which includes administering to a patient an agent which modulates Mina53 or NO66 oxygenase activity. Such agents may include inhibitors of Mina53 or NO66 oxygenase activity. In view of the role that Mina53 or NO66 may play in translational accuracy, such agents may be used for the treatment of diseases caused by premature stop-codons, such as cystic fibrosis (CF), haemophilia, retinitis pigmentosa and Duchene muscular dystrophy (DMD). Such agents may also be used to combat retroviruses, such as HIV.

A therapeutically effective amount of an agent is typically administered to a subject in need thereof.

In various further aspects, the present invention thus enable the development of pharmaceutical compositions, medicaments, drugs or other compositions for such a purpose, the composition comprising one or more agents, compounds or substances as described herein, including inhibitors of Mina53 or NO66 oxygenase activity, the use of such a composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients. Typically such agents are useful as anti-microbial agents, for example for use as antibiotics to treat bacterial infection in an individual.

In one embodiment the method for providing a pharmaceutical composition may typically comprise:
(a) identifying an agent by an assay method of the invention; and
(b) formulating the agent thus identified with a pharmaceutically acceptable excipient.

The pharmaceutical compositions of the invention may comprise an agent, polypeptide, polynucleotide, vector or antibody according to the invention and a pharmaceutically acceptable excipient.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

All the documents cited herein are incorporated herein by reference.

The following Examples illustrate the invention.

EXAMPLES

Mina53 and NO66 Purification

Human Mina53 and NO66 full-length cDNA image clones were purchased from Souce BioScience LifeScience. Truncated constructs Mina53 (A26-V465) and NO66 (A116-N641) were produced as N-terminally hexa-His tagged pET28a proteins using vectors and standard method. To induce expression, 0.5 mM isopropyl beta-D-1-thiogalactopyranoside (IPTG) was added to cultures at $OD_{600}$=0.6, and growth then continued for 16 h at 15° C. Purification of Mina53 and NO66 was carried out by standard procedures using the standard His-tag affinity chromatography following the GE Healthcare instructions of the column manufactions.

Mina53 and NO66 Stable Cell Lines

Doxycycline-inducible Mina53 overexpressing cells were made by a standard procedure as follows. The human Mina53 gene was amplified by PCR and sub-cloned into pUHD10 with an N-terminal 3×-FLAG tag using standard procedures. Stable transfectants were generated from U-2OS cells bearing the reverse tetracycline responsive transactivator and a tetKRAB silencer construct by transfection with the pUHD10 vector alone or pUHD10-Mina53 in combination with pcDNA3.1 using Fugene6 (Roche). 48 hours after transfection, cells were separated onto 10 cm dishes and treated with neomycin (1 mg/ml, G418) for 2-3 weeks. Independent clones were picked and tested for doxycycline inducible gene expression.

Stable overexpressing NO66 cells were made as follows. The human NO66 gene was amplified by PCR and sub-cloned into pEF6 with an N-terminal HA-tag using standard procedures. Stable transfectants were generated from HEK293T cells by transfection with pEF6 vector alone, or pEF6-NO66 in combination with pBabe PURO using Fugene6. 48 hours after transfection, cells were treated with Puromycin (1 ug/ml) for 2-3 weeks until a stable pool was selected.

Doxycycline-inducible NO66 ShRNA knockdown cells were made as follows. Control sequence primers, #8 sequence primers. Sequences were cloned into the EcoRI/XhoI sites of a modified pTRIPZ vector (Open Biosystems) in which the Puromycin resistance cassette was replaced with a Blasticidin resistance cassette (pTRIBZ). Lentiviral pTRIBZ control ShRNA (FF3) or NO66 ShRNA (#8) particles were used to infect A549 lung adenocarcinoma and HeLa cervical carcinoma cells for 24 hours prior to selection in 5 μg/ml Blasticidin. Cells were treated with 2 μg/ml Doxycycline for 12 days prior to ribosome purification HPLC and MS analyses (see below).

Preparation of Extracts for Proteomic Analyses

A typical procedure is described as follows. Extracts from $1 \times 10^8$ (eg. HEK 293T Cells) cells were prepared in lysis buffer (10 mM Tris/HCl pH 7.5, 300 mM NaCl, 0.5% NP40 supplemented with Complete Protease Inhibitor Cocktail (Roche)). After centrifugation supernatants were incubated with either anti-FLAG agarose resin (Mina53 pulldown; from Sigma) or anti-HA agarose resin (NO66 pulldown; from Sigma) for 1 hour at 4° C. with constant rotation. After centrifugation the supernatant was removed, the beads washed three times wash buffer (10 mM Tris/HCl pH 7.5, 300 mM NaCl, 0.5% NP40) and the proteins were eluted in SDS-sample buffer and subjected to SDS-PAGE and coomassie blue staining.

Protein Analysis by Mass Spectrometry

A typical procedure is described below. Proteins were separated by 1D SDS-PAGE and stained by using the Colloidal Blue Staining Kit (Invitrogen). Protein bands were excised and digested with trypsin (Promega) according to published protocols.

The digested material was subjected to nano-ultra performance liquid chromatography tandem MS analysis (nano-UPLC-MS/MS) using a 75 μm-inner diameter×25 cm $C_{18}$ nanoAcquity™ UPLC™ column (1.7-μm particle size; Waters) and a 90 min gradient of 2-45% solvent B (solvent A: 99.9% $H_2O$, 0.1% HCOOH acid; solvent B: 99.9% MeCN, 0.1% HCOOH acid) using a Waters nanoAcquity UPLC system (final flow rate, 250 nl/min; 7000 p.s.i.) coupled to a Q-TOF Premier tandem mass spectrometer (Waters) run in positive ion mode. MS analyses were performed in data-directed analysis (DDA) mode (MS to MS/MS switching at precursor ion counts greater than 10 and MS/MS collision energy dependent on precursor ion mass and charge state). All raw MS data were processed using the PLGS software (version 2.3) including deisotoping and deconvolution (converting masses with multiple charge states to m/z=1). The mass accuracy of the raw data was calibrated using Glu-fibrinopeptide (200 fmol/μl; 700 nl/min flow rate; 785.8426 Da $[M+2H]^{2+}$) that was infused into the mass spectrometer as a lock mass during analysis. MS and MS/MS data were calibrated at intervals of 30 s. MS/MS spectra (peak lists) were searched against the UniProtKB/Swiss-Prot database (Version 2010 Jul. 16; 518,415 sequences) database using Mascot version Fe. 3, 2001 (Matrix Science) and the following parameters: peptide tolerance, 0.2 Da; $^{13}C$=1; fragment tolerance, 0.1 Da; missed cleavages, 2; instrument type, ESI-Q-TOF; fixed modification, carbamidomethylation (C); and variable modifications, deamidation (N,Q) and oxidation (M, H, W). Analytical runs were repeated with an inclusion list for identified peptides with the highest ion score if histidinyl hydroxylation was detected. The interpretation and presentation of MS/MS data were performed according to published guidelines. Assignments of hydroxylation on histidinyl sites identified by Mascot were verified by manual inspection. Ion chromatograms were extracted using the mass windows of ±0.1 Da.

NMR Analyses

NMR-analyses used a Bruker AVIII 700 system equipped with an inverse TCI cryoprobe optimised for $^1H$ observation and running TOPSPIN 2 software. Chemical shifts are reported in ppm relative to $D_2O$ ($\delta_H$ 4.72); the deuterium signal was used as an internal lock signal and the HDO signal was reduced by presaturation where necessary.

Enzyme Activity Assays

Hydroxylation Assay by MALDI-TOF MS:

Assay mixtures (final volume 20 μL in 50 mMHEPES, 500 mMNaCl, 5-10% glycerol, 0.5 mM Tris(2-carboxyethyl) phosphine hydrochloride pH 7.5) contained: enzyme (10 μM), substrate (100 μM), 2OG (200 μM), Fe(II) (100 μM) and ascorbate (100 uM). The reaction mixture was incubated at 37° C. for 30 minutes. The reaction mixture was then placed on ice, 10 μl of 1% formic acid was added to quench the reaction, and the mixture was centrifuged to separate insoluble material that precipitated. The resultant soluble mixture (1 μl) and α-cyano-4-hydroxycinnamic acid (CHCA) matrix solution (1 μl) (LaserBio Labs) were double spotted onto a 96 well MALDI sample plate, and when dry analysed using MALDI-TOF MS on a Waters Micromass™ MALDI micro MX™ mass spectrometer in negative ion reflectron mode.

Synthesis and Purification of Peptides

Peptides were synthesized using a Multipep peptide synthesis machine (Intavis AG Bioanalytical Instruments, Germany) using Fmoc-protected amino acids on a Tentagel S-RAM resin and DIC/HOBT coupling strategy and deprotected by 2.5% triisopropylsilane/97.5% CF3COOH(TFA) for three hours. The peptides GRGNAGGLHHHRINFD-KYHP (SEQ ID NO:6) and HPFGGGNHQHIGKPSTIRRD (SEQ ID NO:8) were synthesized on a CS Bio Co 336x peptide synthesizer using similar methods and purified by reverse phase HPLC.

Alanine Scanning Assays

The importance of individual residues in peptides GRG-NAGGLHHHRINFDKYHP (SEQ ID NO:6) and HPFGGGNHQHIGKPSTIRRD (SEQ ID NO:8) was tested by Alanine substitution studyies assay. Each residues at was systematically replaced with an alanine except where an alanine was already present) using the same protocol for enzyme activity assays as described above. The results revealed that for the RpL27a peptide, the H11, R12 and I13 residues are important or essential for activity and for the RpL8 peptide N7 and H10 are important residues.

Assignment of Hydroxy-His 39 RPL27A and Hydroxy-His 216 RPL8

Ribosomes were isolated from HEK293T using well-established protocols described in by Madjar (Cell Biology: A Laboratory Handbook (J. E. Celis, ed) pp. 657-661 Academic Press, New York) and Belin (Curr. Protoc. Cell Biol.: Unit 3.40, 2010). Essentially, contaminating non-ribosomal proteins and RNA molecules were removed by cell fractionation to produce a post-mitochondrial supernatant that was passed through a sucrose cushion at 100,000×g for 4 h in a Beckmann ultracentrifuge (SW-28 rotor) in order to sediment purified ribosomal complexes. Proteins were extracted from the ribosomal pellet by addition of magnesium chloride and glacial acetic and precipitated by addition of acetone.

To separate RPL8 and RPL27A from the ribosomal preparation an HPLC method was employed. Acetone precipitated, lyophilised protein pellets were resuspended in 2% glacial acetic acid, prior to separation on an Agilent 1200 system with a Vydac 214TP column (250×4.6 mm, particle size 5 μm. Reversed phase separation of RPL27A used a mobile phase of buffer A (buffer A: 0.1% trifluoroacetic acid in water) and buffer B (0.08% trifluoroacetic acid in acetonitrile). The flow rate was set at 1 mL/min with the following gradient optimised for the separation of RPL8 and RPL27A: 0.01 min-10% B; 10 min-10% B; 25 min-20% B; 180 min-43% B; 185 min-95% B. All experiments were performed at room temperature with the UV detector set at 214 nm. Under these assay conditions, RPL8 eluted at 102-104 min and RPL27A at 112-114 min. Fractions containing Rpl8 and RPL27A were lyophilised by vacuum centrifugation, prior to solubilisation in Laemmli sample buffer and SDS-PAGE analysis followed by Coomassie Blue staining. Species corresponding to RPL8 and RPL27A were subject to in-gel proteolysis with trypsin according to published protocols (Batycka, Inglis et al. 2006). The digested material was subjected to nano-UPLC MS/MS (nanoAcquity UPLC coupled to a Q-T of Premier tandem mass spectrometer; Waters) run in positive ion mode.

Results

FIG. 1 shows the sequence alignment of human FIH, Mina53 and NO66. Human FIH (gi|32129605), Mina53 (gi|23307412) and NO66 (gi|106879206) sequences were aligned and shaded using ClustalW and BoxShade servers.

FIG. 2 shows the results of Mina53 and NO66 proteomic pulldowns. A) Extracts from doxycycline-treated U2OS cells overexpressing FLAG-tagged Mina53 were immunoprecipitated with anti-FLAG antibody coupled affinity agarose. FLAG complexes were washed in lysis buffer, eluted in Laemmli buffer and separated by SDS-PAGE prior to coomassie blue staining. Co-precipitating proteins were identified by in-gel trypsinolysis and MS. B) Extracts from HEK293T cells stably overexpressing HA-tagged NO66 were immunoprecipitated with anti-HA antibody coupled affinity agarose. NO66 complexes were washed in lysis buffer, eluted in Laemmli buffer and separated by SDS-PAGE prior to coomassie blue staining. Co-precipitating proteins were identified by in-gel trypsinolysis and MS.

Figure 3:
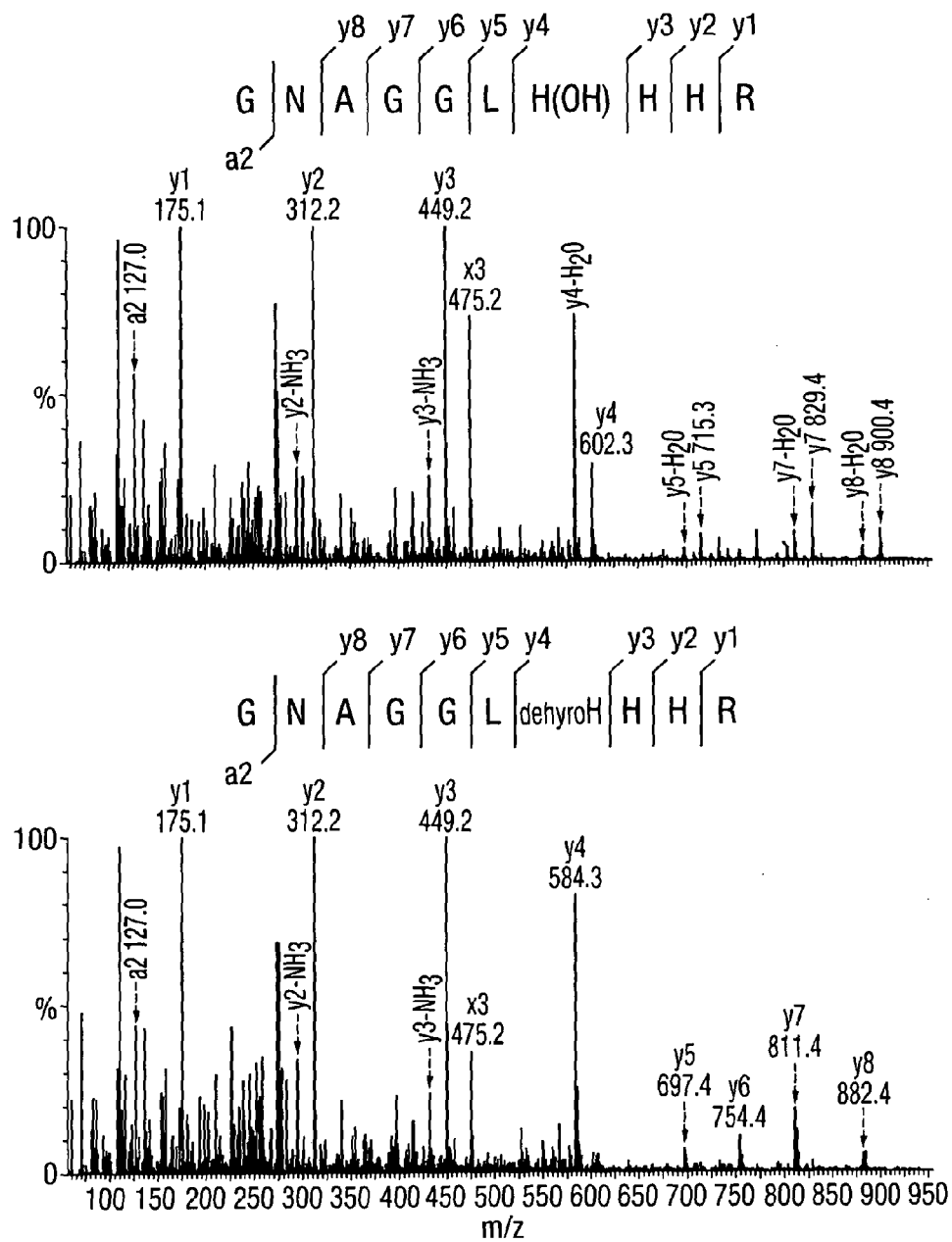
FIG. 3: RpL27a31-50 peptide is a Mina53 substrate in vitro. RpL27a31-50 peptide (GRGNAGGLHHHRINFD-KYHP) (SEQ ID NO:6) incubated in the presence of recombinant Mina53 displayed a 16 Da increase in mass as determined by MALDI-TOF analyses (data not show). A) LCMS and B) MSMS spectra of the tryptic peptide GNAGGLHHHR (SEQ ID NO:7). The hydroxlated species exhibits a +16 Da mass shift on the y-ion series appearing at y4, thus assigning hydroxylation to H39. A −2 Da shift mass shift was commonly observed on fragment ions containing hydroxy-histidine.

FIG. 3 demonstrates that RpL27a31-50 peptide is a Mina53 substrate in vitro. RpL27a31-50 peptide (GRGNAGGLHHHRINFDKYHP) (SEQ ID NO: 6) incubated in the presence of recombinant Mina53 displayed a 16 Da increase in mass as determined by MALDI-TOF analyses (data not show). A) LCMS and B) MSMS spectra of the tryptic peptide GNAGGLHHHR (SEQ ID NO:7). The hydroxlated species exhibits a +16 Da mass shift on the y-ion series appearing at y4, thus assigning hydroxylation to H39. A −2 Da shift mass shift was commonly observed on fragment ions containing hydroxy-histidine.

Figure 4:
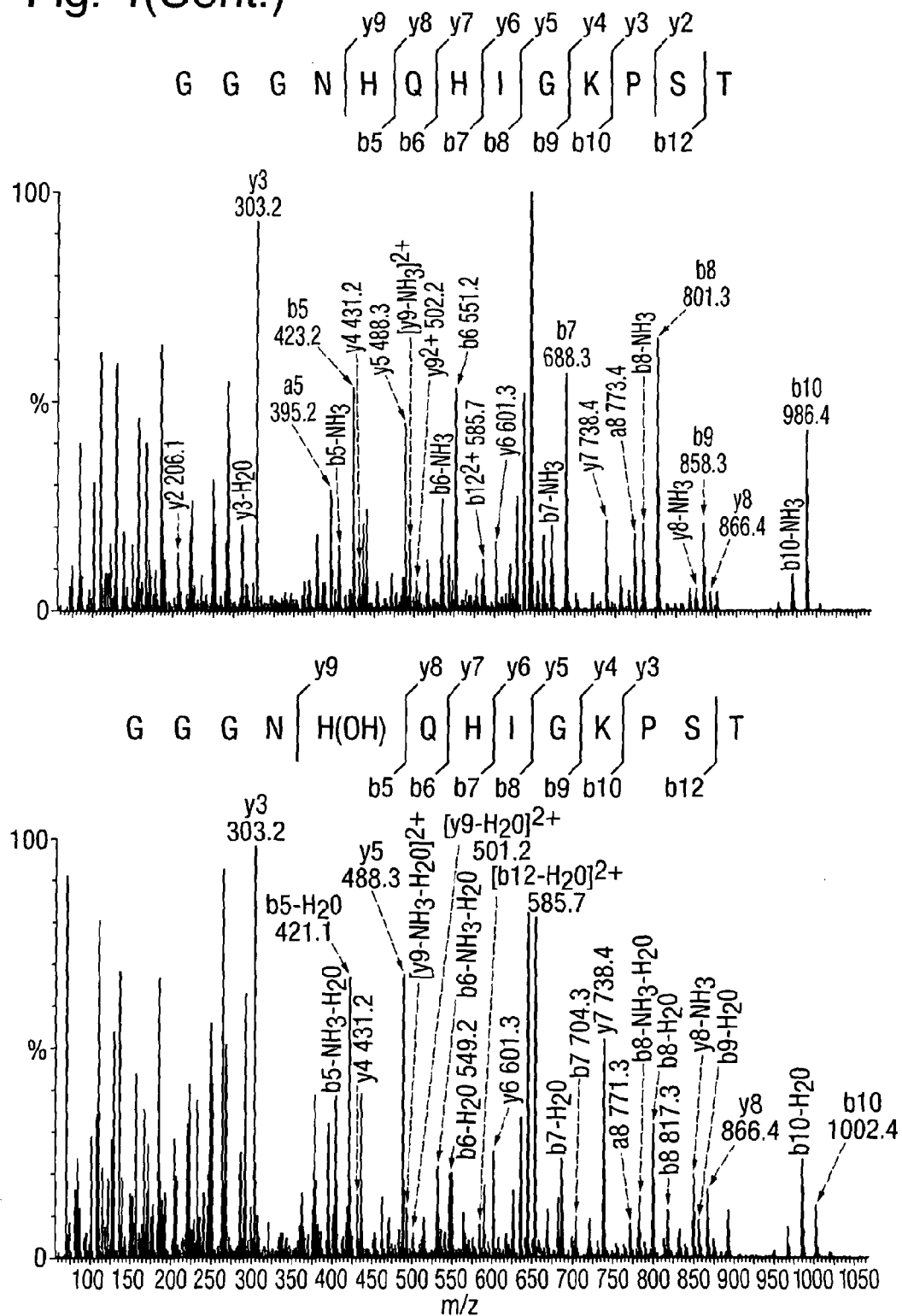
FIG. 4: RpL8 208-227 peptide is NO66 substrate in vitro. RpL8 209-228 peptide (HPFGGGNHQHIGKPSTIRRD) (SEQ ID NO:8) incubated in the presence of recombinant NO66 displayed 16 Da increase in mass as determined by MALDI-TOF analyses (data not show). A) LCMS and B) MSMS spetra of chymotryptic peptide GGGNHQHIGKPST (SEQ ID NO:9). The hydroxlated species exhibits a +16 Da mass shift on the y-ion series appearing at y13, thus assigning hydroxylation to H216. A −2 Da shift mass shift was commonly observed on fragment ions containing hydroxyl-histidine.

FIG. 4 demonstrates that RpL8 208-227 peptide is NO66 substrate in vitro. RpL8 209-228 peptide (HPFGGGNHQHIGKPSTIRRD) (SEQ ID NO:8) incubated in the presence of recombinant NO66 displayed 16 Da increase in mass as determined by MALDI-TOF analyses (data not show). A) LCMS and B) MSMS spetra of chymotryptic peptide GGGNHQHIGKPST (SEQ ID NO:9). The hydroxlated species exhibits a +16 Da mass shift on the y-ion series appearing at y13, thus assigning hydroxylation to H216. A −2 Da shift mass shift was commonly observed on fragment ions containing hydroxyl-histidine.

Figure 5:
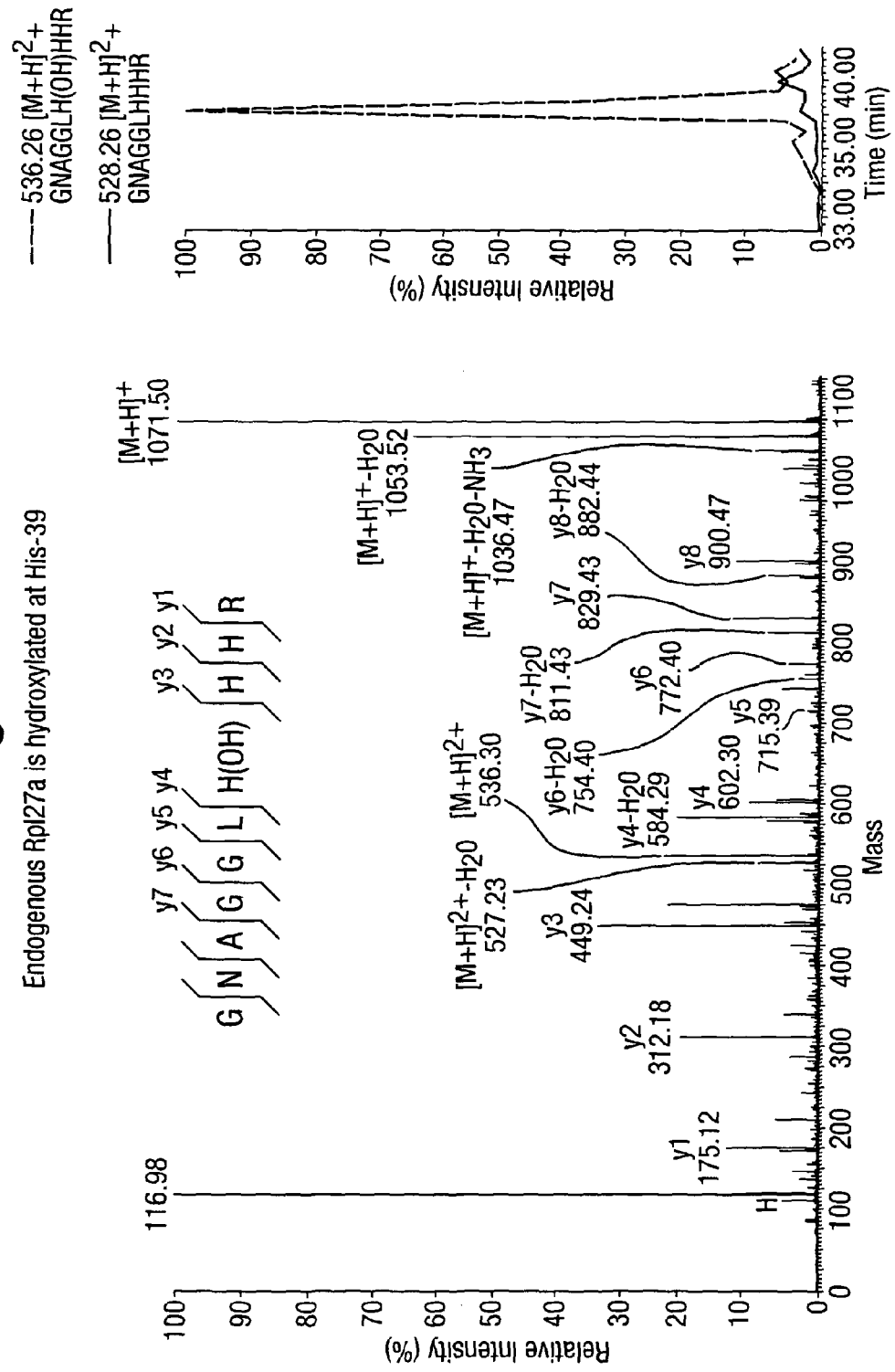
FIG. 5: Endogenous RpL27a is hydroxylated at H39. A) MSMS—Ribosomal proteins were purified from HEK293T cell extracts as described. Rpl27a was separated from other ribosomal proteins by HPLC, lyophilized and subject to SDS-PAGE and coomassie blue staining prior to in-gel trypsinolysis and MSMS analysis.

FIG. 5 demonstrates that endogenous RpL27a is hydroxylated at H39. A) MSMS-Ribosomal proteins were purified from HEK293T cell extracts as described. Rpl27a was separated from other ribosomal proteins by HPLC, lyophilized and subject to SDS-PAGE and coomassie blue staining prior to in-gel trypsinolysis and MSMS analysis.

FIG. 6 demonstrates that endogenous Rpl8 H216 hydroxylation is dependent on NO66. Ribosomal proteins were purified from doxycyline-treated doxycycline-inducible pTRIBZ control ShRNA or NO66 ShRNA A549 and HeLa cells as described. Rpl8 was separated from other ribosomal proteins by HPLC, lyophilized and subject to in-solution trypsinolysis and MS analysis. A) MSMS spectra of the unhydroxylated (left) and hydroxylated (right) GVAMNPVEHPFGGGNHQHIGKPSTIR (SEQ ID NO:10) tryptic peptides. The hydroxlated species exhibits a +16 Da mass shift on the y-ion series appearing at y16, thus assigning hydroxylation to H216. B) i) LC-MS spectra of unoxidised and oxidized GVAMNPVEHPFGGGNHQHIGKPSTIR (SEQ ID NO:10) tryptic peptides from control ShRNA A549 cells. ii) LC-MS spectra of unoxidised and oxidized GVAMNPVEHPFGGGNHQHIGKPSTIR (SEQ ID NO:10) tryptic peptides from NO66 ShRNA A549 cells. C) i) LC-MS spectra of unoxidised and oxidized GVAMNPVEHPFGGGNHQHIGKPSTIR (SEQ ID NO:10) tryptic peptides from control ShRNA HeLa cells. ii) LC-MS spectra of unoxidised and oxidized GVAMNPVEHPFGGGNHQHIGKPSTIR (SEQ ID NO:10) tryptic peptides from NO66 ShRNA HeLa cells.

The His hydroxylation of Mina 53 was further investigated. Mina53 catalyzed His-hydroxlation occurs at the beta-position. Hydroxylated peptide RpL27a31-50 (GRGNAGGLHHRINFDKYHP (SEQ ID NO:6)) was produced by incubation with Mina53 under standard assay conditions (hydroxylated to ~95% as tested by MALDI-TOF analyses), HPLC purified and analysed using an NMR 700 spectroscope. 2D $^1$H-$^1$H COSY spectrum of the spectrum of the hydroxylated RpL27a31-50 peptide in $D_2O$ indicating the $^1$H-$^1$H correlation between the resonances arising from the a- and b-hydrogens (data not shown).

The His-hydroxylation of NO66 was further investigated. NO66 catalyzed His-hydroxlation occurs at the beta-position. Hydroxylated peptide RpL8 209-228 peptide (HPFGGGNHQHIGKPSTIRRD) (SEQ ID NO:8) was produced by incubation with NO66 under standard assay conditions (hydroxylated to ~85% as tested by MALDI-TOF analyses), HPLC purified and analysed using an NMR 700 spectroscope. 2D $^1$H-$^1$H COSY spectrum of the spectrum of the hydroxylated Rpl8 209-228 peptide in $D_2O$ indicating the $^1$H-$^1$H correlation between the resonances arising from the a- and b-hydrogens (data not shown).

The invention claimed is:

1. A method for assaying Mina53 or NO66 activity, the method comprising contacting a peptide comprising a histidinyl residue with a Mina53 or NO66 polypeptide and determining whether the histidinyl residue in said peptide is hydroxylated wherein the method is carried out in the presence of Fe(II) and 2-oxoglutarate (2OG).

2. A method according to claim 1, wherein said peptide comprises a ribosomal protein.

3. The method according to claim 1, wherein the peptide is one or both at the human ribosomal proteins Rpl27a and Rpl8 respectively.

4. The method according to claim 1, wherein the peptide comprises:
   (a) the amino acid sequence of SEQ ID NO: 4 or SEQ ID NO: 5;
   (b) a variant thereof having at least 60% identity to SEQ ID NO: 4 and SEQ ID NO: 5 and comprising a histidine equivalent to histidine at position 39 of SEQ ID NO: 4 or position 216 of SEQ ID NO: 5; or
   (c) a fragment of (a), or (b) of at least 6 amino acids in length and comprising a histidine at positions 39 and 216 of SEQ ID NO: 4 and SEQ ID NO: 5.

5. The method according to claim 1, wherein the method is carried out in the presence of a reducing agent.

6. The method according to claim 1, wherein the Mina53 or NO66 polypeptide comprises:
   (a) the amino acid sequence of SEQ ID NO: 1 or SEQ ID NO: 2
   (b) a variant thereof having at least 60% identity thereto and having histidinyl hydroxylase activity; or is a fragment of either thereof having histidinyl hydroxylase activity.

7. The method according to claim 1, wherein the assay is carried out in the presence of a test agent to determine whether the test agent is a modulator of Mina53 or NO66 activity.

8. A method for identifying an inhibitor of Mina53 or NO66 oxygenase activity, the method comprising contacting a Mina53 or NO66 polypeptide and histidine containing peptides with a test agent under conditions suitable for oxygenase activity, and monitoring for hydroxylation of the histidine of said peptide to give a S-3-hydroxyhistidinyl residue, wherein the method is carried out in the presence of Fe(II) and 2-oxoglutarate (2OG).

9. The method according to claim 7, wherein the test agent is a reported inhibitor of a 2OG oxygenase other than Mina53 or NO66, or an analogue or variant of such an inhibitor.

10. The method of claim 9, wherein the inhibitor is a known 2OG-oxgenase inhibitor selected from an N-oxalyl amino acid, N-oxalylglycine or a derivative thereof, a glycine or alanine derivative, a 2-oxoacid analogue, a flavonoid or flavonoid derivative, or genistein.

11. The method of claim 7, wherein the method further comprises determining whether the test agent modulates the activity of a 2-oxoglutarate dependent oxygenase other than Mina53 or NO66, thereby determining whether the test agent selectively modulates the activity of the 2-oxoglutarate dependent oxygenase other than Mina53 or NO66.

* * * * *

SEQUENCE LISTING

<160> NUMBER OF SEQ ID NOS: 12

<210> SEQ ID NO 1
<211> LENGTH: 465
<212> TYPE: PRT
<213> ORGANISM: Homo sapiens

<400> SEQUENCE: 1

Met Pro Lys Lys Ala Lys Pro Thr Gly Ser Gly Lys Glu Glu Gly Pro
1               5                   10                  15

Ala Pro Cys Lys Gln Met Lys Leu Glu Ala Ala Gly Gly Pro Ser Ala
            20                  25                  30

Leu Asn Phe Asp Ser Pro Ser Ser Leu Phe Glu Ser Leu Ile Ser Pro
        35                  40                  45

Ile Lys Thr Glu Thr Phe Phe Lys Glu Phe Trp Glu Gln Lys Pro Leu
50                  55                  60

Leu Ile Gln Arg Asp Asp Pro Ala Leu Ala Thr Tyr Tyr Gly Ser Leu
65                  70                  75                  80

Phe Lys Leu Thr Asp Leu Lys Ser Leu Cys Ser Arg Gly Met Tyr Tyr
                85                  90                  95

Gly Arg Asp Val Asn Val Cys Arg Cys Val Asn Gly Lys Lys Lys Val
            100                 105                 110

Leu Asn Lys Asp Gly Lys Ala His Phe Leu Gln Leu Arg Lys Asp Phe
        115                 120                 125

Asp Gln Lys Arg Ala Thr Ile Gln Phe His Gln Pro Gln Arg Phe Lys
130                 135                 140

Asp Glu Leu Trp Arg Ile Gln Glu Lys Leu Glu Cys Tyr Phe Gly Ser
145                 150                 155                 160

Leu Val Gly Ser Asn Val Tyr Ile Thr Pro Ala Gly Ser Gln Gly Leu
                165                 170                 175

Pro Pro His Tyr Asp Asp Val Glu Val Phe Ile Leu Gln Leu Glu Gly
            180                 185                 190

Glu Lys His Trp Arg Leu Tyr His Pro Thr Val Pro Leu Ala Arg Glu
        195                 200                 205

Tyr Ser Val Glu Ala Glu Arg Ile Gly Arg Pro Val His Glu Phe
210                 215                 220

Met Leu Lys Pro Gly Asp Leu Leu Tyr Phe Pro Arg Gly Thr Ile His
225                 230                 235                 240

Gln Ala Asp Thr Pro Ala Gly Leu Ala His Ser Thr His Val Thr Ile
                245                 250                 255

Ser Thr Tyr Gln Asn Asn Ser Trp Gly Asp Phe Leu Leu Asp Thr Ile
            260                 265                 270

Ser Gly Leu Val Phe Asp Thr Ala Lys Glu Asp Val Glu Leu Arg Thr
        275                 280                 285

Gly Ile Pro Arg Gln Leu Leu Gln Val Glu Ser Thr Thr Val Ala
290                 295                 300

Thr Arg Arg Leu Ser Gly Phe Leu Arg Thr Leu Ala Asp Arg Leu Glu
305                 310                 315                 320

Gly Thr Lys Glu Leu Leu Ser Ser Asp Met Lys Lys Asp Phe Ile Met
                325                 330                 335

His Arg Leu Pro Pro Tyr Ser Ala Gly Asp Gly Ala Glu Leu Ser Thr
            340                 345                 350

Pro Gly Gly Lys Leu Pro Arg Leu Asp Ser Val Val Arg Leu Gln Phe
        355                 360                 365

```
Lys Asp His Ile Val Leu Thr Val Leu Pro Asp Gln Asp Gln Ser Asp
    370                 375                 380

Glu Ala Gln Glu Lys Met Val Tyr Ile Tyr His Ser Leu Lys Asn Ser
385                 390                 395                 400

Arg Glu Thr His Met Met Gly Asn Glu Glu Thr Glu Phe His Gly
                405                 410                 415

Leu Arg Phe Pro Leu Ser His Leu Asp Ala Leu Lys Gln Ile Trp Asn
                420                 425                 430

Ser Pro Ala Ile Ser Val Lys Asp Leu Lys Leu Thr Thr Asp Glu Glu
                435                 440                 445

Lys Glu Ser Leu Val Leu Ser Leu Trp Thr Glu Cys Leu Ile Gln Val
450                 455                 460

Val
465

<210> SEQ ID NO 2
<211> LENGTH: 641
<212> TYPE: PRT
<213> ORGANISM: Homo sapiens

<400> SEQUENCE: 2

Met Asp Gly Leu Gln Ala Ser Ala Gly Pro Leu Arg Gly Arg Pro
1               5                   10                  15

Lys Arg Arg Lys Pro Gln Pro His Ser Gly Ser Val Leu Ala Leu
                20                  25                  30

Pro Leu Arg Ser Arg Lys Ile Arg Lys Gln Leu Arg Ser Val Val Ser
                35                  40                  45

Arg Met Ala Ala Leu Arg Thr Gln Thr Leu Pro Ser Glu Asn Ser Glu
50                  55                  60

Glu Ser Arg Val Glu Ser Thr Ala Asp Asp Leu Gly Asp Ala Leu Pro
65                  70                  75                  80

Gly Gly Ala Ala Val Ala Ala Val Pro Asp Ala Ala Arg Arg Glu Pro
                85                  90                  95

Tyr Gly His Leu Gly Pro Ala Glu Leu Leu Glu Ala Ser Pro Ala Ala
                100                 105                 110

Arg Ser Leu Gln Thr Pro Ser Ala Arg Leu Val Pro Ala Ser Ala Pro
                115                 120                 125

Pro Ala Arg Leu Val Glu Val Pro Ala Ala Pro Val Arg Val Val Glu
                130                 135                 140

Thr Ser Ala Leu Leu Cys Thr Ala Gln His Leu Ala Ala Val Gln Ser
145                 150                 155                 160

Ser Gly Ala Pro Ala Thr Ala Ser Gly Pro Gln Val Asp Asn Thr Gly
                165                 170                 175

Gly Glu Pro Ala Trp Asp Ser Pro Leu Arg Arg Val Leu Ala Glu Leu
                180                 185                 190

Asn Arg Ile Pro Ser Ser Arg Arg Ala Ala Arg Leu Phe Glu Trp
                195                 200                 205

Leu Ile Ala Pro Met Pro Pro Asp His Phe Tyr Arg Arg Leu Trp Glu
            210                 215                 220

Arg Glu Ala Val Leu Val Arg Arg Gln Asp His Thr Tyr Tyr Gln Gly
225                 230                 235                 240

Leu Phe Ser Thr Ala Asp Leu Asp Ser Met Leu Arg Asn Glu Glu Val
                245                 250                 255

Gln Phe Gly Gln His Leu Asp Ala Ala Arg Tyr Ile Asn Gly Arg Arg
                260                 265                 270
```

-continued

Glu Thr Leu Asn Pro Pro Gly Arg Ala Leu Pro Ala Ala Ala Trp Ser
            275                 280                 285

Leu Tyr Gln Ala Gly Cys Ser Leu Arg Leu Leu Cys Pro Gln Ala Phe
290                 295                 300

Ser Thr Thr Val Trp Gln Phe Leu Ala Val Leu Gln Glu Gln Phe Gly
305                 310                 315                 320

Ser Met Ala Gly Ser Asn Val Tyr Leu Thr Pro Pro Asn Ser Gln Gly
                325                 330                 335

Phe Ala Pro His Tyr Asp Asp Ile Glu Ala Phe Val Leu Gln Leu Glu
                340                 345                 350

Gly Arg Lys Leu Trp Arg Val Tyr Arg Pro Arg Val Pro Thr Glu Glu
            355                 360                 365

Leu Ala Leu Thr Ser Ser Pro Asn Phe Ser Gln Asp Asp Leu Gly Glu
370                 375                 380

Pro Val Leu Gln Thr Val Leu Glu Pro Gly Asp Leu Leu Tyr Phe Pro
385                 390                 395                 400

Arg Gly Phe Ile His Gln Ala Glu Cys Gln Asp Gly Val His Ser Leu
                405                 410                 415

His Leu Thr Leu Ser Thr Tyr Gln Arg Asn Thr Trp Gly Asp Phe Leu
                420                 425                 430

Glu Ala Ile Leu Pro Leu Ala Val Gln Ala Ala Met Glu Glu Asn Val
            435                 440                 445

Glu Phe Arg Arg Gly Leu Pro Arg Asp Phe Met Asp Tyr Met Gly Ala
450                 455                 460

Gln His Ser Asp Ser Lys Asp Pro Arg Arg Thr Ala Phe Met Glu Lys
465                 470                 475                 480

Val Arg Val Leu Val Ala Arg Leu Gly His Phe Ala Pro Val Asp Ala
                485                 490                 495

Val Ala Asp Gln Arg Ala Lys Asp Phe Ile His Asp Ser Leu Pro Pro
            500                 505                 510

Val Leu Thr Asp Arg Glu Arg Ala Leu Ser Val Tyr Gly Leu Pro Ile
515                 520                 525

Arg Trp Glu Ala Gly Glu Pro Val Asn Val Gly Ala Gln Leu Thr Thr
530                 535                 540

Glu Thr Glu Val His Met Leu Gln Asp Gly Ile Ala Arg Leu Val Gly
545                 550                 555                 560

Glu Gly Gly His Leu Phe Leu Tyr Tyr Thr Val Glu Asn Ser Arg Val
                565                 570                 575

Tyr His Leu Glu Glu Pro Lys Cys Leu Glu Ile Tyr Pro Gln Gln Ala
                580                 585                 590

Asp Ala Met Glu Leu Leu Leu Gly Ser Tyr Pro Glu Phe Val Arg Val
            595                 600                 605

Gly Asp Leu Pro Cys Asp Ser Val Glu Asp Gln Leu Ser Leu Ala Thr
610                 615                 620

Thr Leu Tyr Asp Lys Gly Leu Leu Leu Thr Lys Met Pro Leu Ala Leu
625                 630                 635                 640

Asn

<210> SEQ ID NO 3
<211> LENGTH: 349
<212> TYPE: PRT
<213> ORGANISM: Homo sapiens

<400> SEQUENCE: 3

Met Ala Thr Ala Ala Glu Ala Val Ala Ser Gly Ser Gly Glu Pro
1               5                   10                  15

Arg Glu Glu Ala Gly Ala Leu Gly Pro Ala Trp Asp Glu Ser Gln Leu
                20                  25                  30

Arg Ser Tyr Ser Phe Pro Thr Arg Pro Ile Pro Arg Leu Ser Gln Ser
            35                  40                  45

Asp Pro Arg Ala Glu Glu Leu Ile Glu Asn Glu Glu Pro Val Val Leu
        50                  55                  60

Thr Asp Thr Asn Leu Val Tyr Pro Ala Leu Lys Trp Asp Leu Glu Tyr
65                  70                  75                  80

Leu Gln Glu Asn Ile Gly Asn Gly Asp Phe Ser Val Tyr Ser Ala Ser
                85                  90                  95

Thr His Lys Phe Leu Tyr Tyr Asp Glu Lys Lys Met Ala Asn Phe Gln
            100                 105                 110

Asn Phe Lys Pro Arg Ser Asn Arg Glu Glu Met Lys Phe His Glu Phe
        115                 120                 125

Val Glu Lys Leu Gln Asp Ile Gln Gln Arg Gly Gly Glu Glu Arg Leu
    130                 135                 140

Tyr Leu Gln Gln Thr Leu Asn Asp Thr Val Gly Arg Lys Ile Val Met
145                 150                 155                 160

Asp Phe Leu Gly Phe Asn Trp Asn Trp Ile Asn Lys Gln Gln Gly Lys
                165                 170                 175

Arg Gly Trp Gly Gln Leu Thr Ser Asn Leu Leu Ile Gly Met Glu
            180                 185                 190

Gly Asn Val Thr Pro Ala His Tyr Asp Glu Gln Gln Asn Phe Phe Ala
        195                 200                 205

Gln Ile Lys Gly Tyr Lys Arg Cys Ile Leu Phe Pro Pro Asp Gln Phe
    210                 215                 220

Glu Cys Leu Tyr Pro Tyr Pro Val His His Pro Cys Asp Arg Gln Ser
225                 230                 235                 240

Gln Val Asp Phe Asp Asn Pro Asp Tyr Glu Arg Phe Pro Asn Phe Gln
                245                 250                 255

Asn Val Val Gly Tyr Glu Thr Val Val Gly Pro Gly Asp Val Leu Tyr
            260                 265                 270

Ile Pro Met Tyr Trp Trp His His Ile Glu Ser Leu Leu Asn Gly Gly
        275                 280                 285

Ile Thr Ile Thr Val Asn Phe Trp Tyr Lys Gly Ala Pro Thr Pro Lys
    290                 295                 300

Arg Ile Glu Tyr Pro Leu Lys Ala His Gln Lys Val Ala Ile Met Arg
305                 310                 315                 320

Asn Ile Glu Lys Met Leu Gly Glu Ala Leu Gly Asn Pro Gln Glu Val
                325                 330                 335

Gly Pro Leu Leu Asn Thr Met Ile Lys Gly Arg Tyr Asn
            340                 345

<210> SEQ ID NO 4
<211> LENGTH: 148
<212> TYPE: PRT
<213> ORGANISM: Homo sapiens

<400> SEQUENCE: 4

Met Pro Ser Arg Leu Arg Lys Thr Arg Lys Leu Arg Gly His Val Ser
1               5                   10                  15

His Gly His Gly Arg Ile Gly Lys His Arg Lys His Pro Gly Gly Arg

```
                20                  25                  30
Gly Asn Ala Gly Gly Leu His His Arg Ile Asn Phe Asp Lys Tyr
            35                  40                  45

His Pro Gly Tyr Phe Gly Lys Val Gly Met Lys His Tyr His Leu Lys
 50                  55                  60

Arg Asn Gln Ser Phe Cys Pro Thr Val Asn Leu Asp Lys Leu Trp Thr
 65                  70                  75                  80

Leu Val Ser Glu Gln Thr Arg Val Asn Ala Ala Lys Asn Lys Thr Gly
                85                  90                  95

Ala Ala Pro Ile Ile Asp Val Val Arg Ser Gly Tyr Tyr Lys Val Leu
               100                 105                 110

Gly Lys Gly Lys Leu Pro Lys Gln Pro Val Ile Val Lys Ala Lys Phe
           115                 120                 125

Phe Ser Arg Arg Ala Glu Glu Lys Ile Lys Ser Val Gly Gly Ala Cys
       130                 135                 140

Val Leu Val Ala
145

<210> SEQ ID NO 5
<211> LENGTH: 257
<212> TYPE: PRT
<213> ORGANISM: Homo sapiens

<400> SEQUENCE: 5

Met Gly Arg Val Ile Arg Gly Gln Arg Lys Gly Ala Gly Ser Val Phe
 1               5                  10                  15

Arg Ala His Val Lys His Arg Lys Gly Ala Ala Arg Leu Arg Ala Val
                20                  25                  30

Asp Phe Ala Glu Arg His Gly Tyr Ile Lys Gly Ile Val Lys Asp Ile
            35                  40                  45

Ile His Asp Pro Gly Arg Gly Ala Pro Leu Ala Lys Val Val Phe Arg
 50                  55                  60

Asp Pro Tyr Arg Phe Lys Lys Arg Thr Glu Leu Phe Ile Ala Ala Glu
 65                  70                  75                  80

Gly Ile His Thr Gly Gln Phe Val Tyr Cys Gly Lys Lys Ala Gln Leu
                85                  90                  95

Asn Ile Gly Asn Val Leu Pro Val Gly Thr Met Pro Glu Gly Thr Ile
           100                 105                 110

Val Cys Cys Leu Glu Glu Lys Pro Gly Asp Arg Gly Lys Leu Ala Arg
       115                 120                 125

Ala Ser Gly Asn Tyr Ala Thr Val Ile Ser His Asn Pro Glu Thr Lys
   130                 135                 140

Lys Thr Arg Val Lys Leu Pro Ser Gly Ser Lys Lys Val Ile Ser Ser
145                 150                 155                 160

Ala Asn Arg Ala Val Val Gly Val Val Ala Gly Gly Gly Arg Ile Asp
                165                 170                 175

Lys Pro Ile Leu Lys Ala Gly Arg Ala Tyr His Lys Tyr Lys Ala Lys
            180                 185                 190

Arg Asn Cys Trp Pro Arg Val Arg Gly Val Ala Met Asn Pro Val Glu
       195                 200                 205

His Pro Phe Gly Gly Gly Asn His Gln His Ile Gly Lys Pro Ser Thr
   210                 215                 220

Ile Arg Arg Asp Ala Pro Ala Gly Arg Lys Val Gly Leu Ile Ala Ala
225                 230                 235                 240
```

```
Arg Arg Thr Gly Arg Leu Arg Gly Thr Lys Thr Val Gln Glu Lys Glu
                245                 250                 255

Asn

<210> SEQ ID NO 6
<211> LENGTH: 20
<212> TYPE: PRT
<213> ORGANISM: Homo sapiens

<400> SEQUENCE: 6

Gly Arg Gly Asn Ala Gly Gly Leu His His His Arg Ile Asn Phe Asp
1               5                   10                  15

Lys Tyr His Pro
            20

<210> SEQ ID NO 7
<211> LENGTH: 10
<212> TYPE: PRT
<213> ORGANISM: Homo sapiens

<400> SEQUENCE: 7

Gly Asn Ala Gly Gly Leu His His His Arg
1               5                   10

<210> SEQ ID NO 8
<211> LENGTH: 20
<212> TYPE: PRT
<213> ORGANISM: Homo sapiens

<400> SEQUENCE: 8

His Pro Phe Gly Gly Gly Asn His Gln His Ile Gly Lys Pro Ser Thr
1               5                   10                  15

Ile Arg Arg Asp
            20

<210> SEQ ID NO 9
<211> LENGTH: 13
<212> TYPE: PRT
<213> ORGANISM: Homo sapiens

<400> SEQUENCE: 9

Gly Gly Gly Asn His Gln His Ile Gly Lys Pro Ser Thr
1               5                   10

<210> SEQ ID NO 10
<211> LENGTH: 26
<212> TYPE: PRT
<213> ORGANISM: Homo sapiens

<400> SEQUENCE: 10

Gly Val Ala Met Asn Pro Val Glu His Pro Phe Gly Gly Gly Asn His
1               5                   10                  15

Gln His Ile Gly Lys Pro Ser Thr Ile Arg
            20                  25

<210> SEQ ID NO 11
<211> LENGTH: 5
<212> TYPE: PRT
<213> ORGANISM: Homo sapiens

<400> SEQUENCE: 11

His His His Arg Ile
1               5
```

```
<210> SEQ ID NO 12
<211> LENGTH: 4
<212> TYPE: PRT
<213> ORGANISM: Homo sapiens

<400> SEQUENCE: 12

Asn His Gln His
1
```